US011767242B2

(12) United States Patent
Roy et al.

(10) Patent No.: US 11,767,242 B2
(45) Date of Patent: Sep. 26, 2023

(54) COMPACT PORTABLE PLASMA REACTOR

(71) Applicant: SURFPLASMA, INC., Gainesville, FL (US)

(72) Inventors: Subrata Roy, Gainesville, FL (US); Sherlie Eileen Portugal Atencio, Doral, FL (US); Alexander Gustaw Schindler-Tyka, Richmond, VA (US)

(73) Assignee: SURFPLASMA, INC., Gainesville, FL (US)

( * ) Notice: Subject to any disclaimer, the term of this patent is extended or adjusted under 35 U.S.C. 154(b) by 424 days.

(21) Appl. No.: 16/860,523

(22) Filed: Apr. 28, 2020

(65) Prior Publication Data
US 2020/0325049 A1    Oct. 15, 2020

Related U.S. Application Data

(63) Continuation-in-part of application No. 16/235,492, filed on Dec. 28, 2018, now Pat. No. 10,651,014.
(Continued)

(51) Int. Cl.
*C02F 1/78* (2023.01)
*A61L 2/20* (2006.01)
(Continued)

(52) U.S. Cl.
CPC .............. *C02F 1/78* (2013.01); *A61L 2/202* (2013.01); *A61L 2/24* (2013.01); *B01F 25/3121* (2022.01);
(Continued)

(58) Field of Classification Search
CPC .... H03F 3/217; H03F 3/68; C02F 1/78; C02F 2201/782; C02F 1/004; C02F 2201/46165; C01B 2201/90; C01B 13/11
See application file for complete search history.

(56) References Cited

U.S. PATENT DOCUMENTS 4,370,785 A * 2/1983 Assenza ................ B06B 1/0622
29/25.35
5,186,841 A * 2/1993 Schick ...................... C02F 1/78
261/36.1
(Continued)

OTHER PUBLICATIONS

Birmingham and Hammerstrom, Bacterial Decontamination Using Ambient Pressure Nonthermal Discharges, Feb. 2000, IEEE Transaction on Plasma Science, vol. 28, No. 1, pp. 51-55 (Year: 2000).*
(Continued)

*Primary Examiner* — Emily P Pham
(74) *Attorney, Agent, or Firm* — SALIWANCHIK, LLOYD & EISENSCHENK

(57) ABSTRACT

Embodiments of the subject invention relate to a small modular self-contained surface plasma device for decontamination of air and surfaces within enclosed volumes. Embodiments of the subject invention relate to a method and apparatus using the technical process of dielectric barrier discharge (DBD) surface plasma generation from ambient atmosphere for decontamination of air and surfaces within enclosed volumes. The primary application mode is for preservation of perishable commodities within industrial shipping containers through reduction of surface spoilage organisms and destruction of evolved gaseous ethylene that causes premature ripening. Additional implementations include deployment for oxidation of surfaces and/or container atmospheres in applications to diminish or eradicate pesticides, toxins, chemical residues, and other natural or introduced contaminants. Other embodiments envisioned include incorporation of device capabilities and or ancillary modules for feedback input (e.g. ozone sensor(s) to maintain steady state levels, self-tuning circuitry to adjust operating frequency), communication (e.g. among modules, RFID data loggers, Wi-Fi output), and programing (e.g. user input of container volume, transit time, ozone level, etc.).

14 Claims, 28 Drawing Sheets

Related U.S. Application Data

(60) Provisional application No. 62/612,027, filed on Dec. 29, 2017.

(51) Int. Cl.

| | | |
|---|---|---|
| *A61L 2/24* | (2006.01) | |
| *C01B 13/11* | (2006.01) | |
| *B01J 19/08* | (2006.01) | |
| *C02F 1/00* | (2023.01) | |
| *H03F 3/21* | (2006.01) | |
| *B01F 25/312* | (2022.01) | |
| *C02F 103/34* | (2006.01) | |
| *C02F 101/20* | (2006.01) | |
| *B01F 101/00* | (2022.01) | |

(52) U.S. Cl.
CPC ............ *B01J 19/088* (2013.01); *C01B 13/115* (2013.01); *C02F 1/008* (2013.01); *H03F 3/21* (2013.01); *A61L 2202/11* (2013.01); *B01F 2101/305* (2022.01); *B01J 2219/0809* (2013.01); *B01J 2219/0875* (2013.01); *B01J 2219/0896* (2013.01); *C02F 2001/007* (2013.01); *C02F 2101/20* (2013.01); *C02F 2103/343* (2013.01); *C02F 2201/782* (2013.01); *C02F 2303/04* (2013.01); *C02F 2303/18* (2013.01)

(56) References Cited

U.S. PATENT DOCUMENTS

| | | | | |
|---|---|---|---|---|
| 6,468,953 | B1* | 10/2002 | Hitchems | A01N 59/00 |
| | | | | 510/505 |
| 6,787,043 | B1* | 9/2004 | Cho | C02F 1/78 |
| | | | | 204/557 |
| 6,841,124 | B2* | 1/2005 | Chien | A61L 2/14 |
| | | | | 422/906 |
| 8,276,888 | B2* | 10/2012 | Osborn | C02F 1/78 |
| | | | | 261/115 |
| 9,059,638 | B2* | 6/2015 | Shen | H02M 3/33507 |
| 9,193,607 | B1* | 11/2015 | Johnston | B01F 25/31231 |
| 9,302,912 | B2* | 4/2016 | Tran | H02M 1/36 |
| 9,585,390 | B2* | 3/2017 | Fridman | A61L 2/16 |
| 9,774,239 | B2* | 9/2017 | Chinga | H02M 1/08 |
| 10,039,850 | B2* | 8/2018 | Taggart | A61L 2/186 |
| 2006/0221536 | A1* | 10/2006 | Goto | B03C 3/08 |
| | | | | 361/231 |
| 2010/0025337 | A1* | 2/2010 | Yencho | C02F 1/325 |
| | | | | 210/243 |
| 2010/0135869 | A1* | 6/2010 | Shiue | C02F 1/4672 |
| | | | | 422/186.08 |
| 2012/0210708 | A1* | 8/2012 | Dunn | G01F 15/063 |
| | | | | 60/494 |
| 2012/0292262 | A1* | 11/2012 | Roy | C02F 1/78 |
| | | | | 210/192 |
| 2014/0008211 | A1* | 1/2014 | Dempster | C01B 13/11 |
| | | | | 422/108 |
| 2014/0065013 | A1* | 3/2014 | Nonnenmacher | A61L 2/202 |
| | | | | 422/24 |
| 2014/0203871 | A1* | 7/2014 | Pamarti | H03F 3/245 |
| | | | | 330/251 |
| 2015/0267727 | A1* | 9/2015 | Segawa | H05H 1/2406 |
| | | | | 313/231.31 |
| 2015/0297768 | A1* | 10/2015 | Bettles | A61L 2/10 |
| | | | | 250/455.11 |
| 2016/0152497 | A1* | 6/2016 | Tandon | C02F 1/50 |
| | | | | 210/130 |
| 2016/0235874 | A1* | 8/2016 | Blakeman | A61L 2/202 |
| 2016/0368753 | A1* | 12/2016 | Bethuy | A47J 31/4403 |
| 2017/0018410 | A1* | 1/2017 | Laux | H01J 37/32541 |
| 2017/0072082 | A1* | 3/2017 | Jurak | A61L 9/20 |
| 2017/0335470 | A1* | 11/2017 | Gykiere | A23B 7/152 |
| 2018/0147308 | A1* | 5/2018 | Koyama | A61L 2/202 |

OTHER PUBLICATIONS

Chinga, Lin and Roy, Self-Tuning High-Voltage High-Frequency Switching Power Amplifier for Asmospheric-Based Plasma Sterilization, Jul. 2014, IEEE Transaction on Plasma Science, vol. 42, No. 7, pp. 1861-1869 (Year: 2014).*

* cited by examiner a b

COMPACT PORTABLE PLASMA REACTOR

CROSS-REFERENCE TO RELATED APPLICATIONS

This application is a continuation-in-part (CIP) of U.S. Ser. No. 16/235,492, filed Dec. 28, 2018, now U.S. Pat. No. 10,651,014, issued May 12, 2020, which claims the priority benefit of U.S. Provisional Application No. 62/612,027, filed Dec. 29, 2017, and this application claims the priority benefit of U.S. Provisional Application Ser. No. 62/832,213, filed Apr. 10, 2019, all of which are incorporated herein by reference in its entirety.

FIELD OF INVENTION

Embodiments relate to a Compact Plasma Reactor (CPR) apparatus and related method. Use of embodiments of the subject CPR and related method can reduce the 12% food waste that occurs annually during the transportation and distribution of perishable products.

BACKGROUND OF INVENTION

Power supply units that drive dielectric barrier discharge devices like plasma actuators and plasma sterilization devices are heavy and bulky weighing several kilograms occupying several square feet of footprint.

According to a 2012 National Resource Defense Council report, forty percent of food in the United States today goes uneaten, representing the equivalent of $165 billion in wasted food each year. Reducing food losses by just 15 percent would be enough food to feed more than 25 million Americans every year at a time when one in six Americans lack a secure supply of food to their tables. Handling issues can occur when perishable commodities experience improper temperatures, such as during transportation delays due to weather, traffic, equipment or vehicle malfunction, or due to congestion at harbors, terminals, or when on loading docks or in warehouses. Imported products can wait days at ports for testing, significantly reducing their shelf life. Industry economic impacts from longer shelf life throughout the distribution chain could be significant to improved industry gross margins and net revenue. Other economic ramifications include job creation, lower health care costs through higher quality and availability of perishables, reduced environmental impacts, and a more productive populace.

Ozone, a major component of atmospheric plasma, is a potent antimicrobial agent. Ozone destroys microorganisms by reacting with oxidizable cellular components, particularly those containing double bonds, sulfhydryl groups, and phenolic rings. Therefore, membrane phospholipids, intracellular enzymes, and genomic material are targeted by ozone; these reactions result in cell damage and death of microorganisms. Ozone offers many advantages as a sterilant/disinfectant gas; ozone is a very efficient sterilant because of its strong oxidizing properties (E=2.076). It also breaks down to harmless oxygen after just a couple of hours, but is active for enough time to effectively kill viruses, bacteria, fungi, and parasites, including those causing food spoilage or human diseases. Efficacy of ozone, however, depends on the target microorganism and the treatment condition. Ozone has been used for sterilization of containers for aseptic packaging, decontamination of fresh produce, and food preservation in cold storage. Ozone is an unstable gas that must be produced on-site, since it cannot be stored, so it is not practical to use in many settings.

Disinfection of drinking water is critical to the protection of public health. Global access to safe water can reduce illness and death from disease, leading to improved health and socioeconomic development.

Systems employing Ozone show great promise in effectively sanitizing drinking water. Ozone ($O_3$), sometimes called "triatomic oxygen", contains three atoms of oxygen. It is a colorless or pale blue gas. Ozone is among the most powerful oxidizing agents known (oxidizing potential 2.07), far stronger than $O_2$. It is unstable at high concentrations, decaying into ordinary oxygen. Its half-life (~20 mins) varies with atmospheric conditions such as temperature, humidity, and air movement. Ozone can be produced as a gas from oxygen in air, or concentrated oxygen. This ozone gas can be dissolved into water, or used in the gas phase for a variety of applications.

Ozone treatment for drinking water is a widely accepted process. Over 3,000 municipal water installations worldwide use ozone as an integral part of the drinking water treatment operations. Major cities include London, Paris, Budapest, Kiev, Moscow and Singapore (Loeb, 2012). In the United States there are nearly 400 ozone drinking water treatment installations. Locations include Atlanta, Boston, Colorado, Dallas, Los Angeles, Milwaukee, New York City, Orlando, and San Diego (Bollyky, 2002; Langlais, 1991; Schulz, 2014).

Two of the city of San Diego's water treatment plants (2018) use ozone as the primary disinfectant. In the city's annual report, they discuss that ozone produces fewer disinfection byproducts than chlorine or chloramines alone and is considered a superior disinfection method. (San Diego Water Report). Furthermore, ozone is GRAS by FDA at 0.4 milligram of ozone per liter of bottled water (O'Donnell, 2012).

The popularity of ozone as a disinfectant is also due to the lack of production of trihalomethanes (THMs) (Richardson, 1999). THMs are formed along with other disinfection by products when chlorine disinfectants used to control microbial contaminants in drinking water react with naturally occurring organic and inorganic matter in water. The major DPB of concern for ozonation is Bromate. Bromate is a byproduct formed by the reaction of ozone with Bromide. Bromide concentrations in surface waters in the United States have typically been quite low, with average values inland ranging from 0.014-0.2 mg/L (VanBriesen). The EPA and WHO have set the maximum contaminant level for bromate in public water systems at 10 ug/L (10 ppb). Treatment plants such as those in San Diego routinely test for Bromate where compliance with the MCL for bromate is determined quarterly on a Running Annual Average (RAA) basis. If the ozone treatment process parameters are adjusted carefully (such as avoiding excessive ozonation), the bromate formation can be limited to levels below the MCL (10 ug/l) in most cases (Bollyky, 2002).

There is a need for systems that do not expose the liquid to excessive concentrations of ozone that would form water disinfection by-products (DBP).

Additionally, with respect to sanitization, data shows that ozone can remove toxic metals such as lead and mercury, emerging compounds such as PFOA/PFOS, and Pharmaceuticals. The removal of pollutants of significant health concerns such as toxic metals, pharmaceuticals, and emerging organic compounds (e.g. perfluorinated alkyl compounds or PFCs) from drinking water sources remains rather challenging as action level limits imposed by regulatory agencies become more and more stringent. Unlike organic pollutants, metals are not biodegradable and their persistence, transformation, and transfer to the food chain lead to negative effects on both ecological functions and human health. Currently, the US-EPA's Priority Pollutant List includes 13 metals: Ag, As, Be, Cd, Cr, Cu, Hg, Ni, Pb, Sb, Se, Tl, and Zn (Adriano, 2001), and regulations are become more stringent with regard to the discharge of metal contaminated water effluents to natural water bodies. A variety of techniques, such as chemical precipitation, coagulation/flocculation and membrane filtration have been used to remove metals from water effluents. However, considerable amount of metals could remain in water effluents as highly stable complexes with organic ligands, therefore, compromising their removal by the above-mentioned methods (Ye et al. 2017). Reliance on the combination of advanced oxidation processes (AOPs) and pH induced precipitation has helped improve the removal of metals such as copper (Cu) from systems containing organic ligands (Huang et al. 2016).

PFCs are persistent, bio-accumulative, and toxic (PBT) chemicals (González-Barreiro et al. 2006), which are now detectable not only in wastewater effluents, but also in a wide variety of environmental matrices. So far, it has been shown that the removal of these pollutants from water resources using traditional water treatment techniques (e.g. ferric or alum coagulation, granular/micro-/ultra-filtration, aeration, oxidation, and disinfection) was mostly ineffective (Appleman et al., 2014). In contrast, anion exchange and granular activated carbon technologies preferably removed longer-chain PFCs while reverse osmosis demonstrated significant removal efficiencies for both short and long chains PFCs (Appleman et al., 2014, McCleaf et al., 2017). However, it is worth noting that the results of some of these studies pointed to unwanted desorption of previously sorbed short chain PFCs during co-removal studies of mixtures of long and short chain PFCs compounds (McCleaf et al., 2017). In 2016, the US-EPA established a lifetime health advisory (LHA) level of 70 ppt (or ng/L) for either individual or combined concentrations of PFOA and PFOS in drinking water. This targeted trace level calls for the need of advanced water treatment processes to remove PFOA and PFOS from drinking water (as source for direct human exposure through water consumption) and wastewater effluents (as potential vector of PFCs to drinking water resources).

Like PFC's, pharmaceuticals are emerging pollutants of growing concern. The standard ways of cleaning water are not designed to snare the tiny amounts of prescription drugs that survive digestion. Concerns have been raised over exposure to pharmaceuticals in drinking water because it is an unintended and involuntary exposure over potentially long periods of time. Ozone-based processes have been shown to reduce the concentration of most pharmaceuticals detected in secondary effluent (Kim et al., 2010).

BRIEF SUMMARY

Embodiments of the subject invention relate to a small modular self-contained surface plasma device for decontamination of air and surfaces within enclosed volumes.

Embodiments of the subject invention relate to a method and apparatus using the technical process of dielectric barrier discharge (DBD) surface plasma generation from ambient atmosphere for decontamination of air and surfaces within enclosed volumes. The primary application mode is for preservation of perishable commodities within industrial shipping containers through reduction of surface spoilage organisms and destruction of evolved gaseous ethylene that causes premature ripening. Additional implementations include deployment for oxidation of surfaces and/or container atmospheres in applications to diminish or eradicate pesticides, toxins, chemical residues, and other natural or introduced contaminants. Other embodiments envisioned include incorporation of device capabilities and or ancillary modules for feedback input (e.g. ozone sensor(s) to maintain steady state levels, self-tuning circuitry to adjust operating frequency), communication (e.g. among modules, RFID data loggers, Wi-Fi output), and programing (e.g. user input of container volume, transit time, ozone level, etc.).

An embodiment of the present invention decontaminates air and surfaces employing a lightweight, portable, modular, small, affordable, low power, low maintenance apparatus, which can be referred to as a Compact Plasma Reactor (CPR), via diffuse electrical plasma generated in atmospheric air. This is accomplished by applying a potential difference between two electrodes, separated by an insulating dielectric layer. It is well known that plasma has adverse effects on living organisms and degrades various chemicals. Ozone is a potent antimicrobial agent, effectively killing viruses, bacteria, fungi, and parasites. Ozone destroys microorganisms by reacting with oxidizable cellular components, particularly those containing double bonds, sulfhydryl groups, and phenolic rings. Therefore, membrane phospholipids, intracellular enzymes, and genomic material are targeted by ozone; these reactions result in cell damage and death of microorganisms. Ozone offers many advantages as a sterilant gas due to strong oxidizing properties ($E=2.076$), but utilization is often not feasible or economical, especially in many transit applications, since it is not stable, cannot be stored and therefore must be generated in situ.

Embodiments of the subject invention have been used to demonstrate that this activity arises primarily from generation of ozone, although contributions from other reactive oxygen species, UV, and other mechanisms may be involved. Ozone naturally decomposes to produce oxygen with no chemical residues. Based on the mechanism of surface plasma-based DBD sterilization, and using empirical analyses, appropriate permutations of operational parameters for effective surface and atmospheric sterilization have been assessed. Embodiments of the subject invention relate to an CPR surface plasma-based ozone generator have properties as a flow actuator that induces a three-dimensional body force to mix ozone with neighboring air for rapid mixing and equalization of ozone levels within the container. Embodiments of the subject invention relate to a microscale portable power amplifier capable of generating plasma across a capacitive load, and can incorporate a switch-mode amplifier capable of producing high-voltage and high-frequency output for plasma generation.

Surface plasma decontamination affords a number of advantages over conventional decontamination methods that employ toxic compounds. Current practices involve use of chlorinating agents, organic acids, hydrogen peroxide or fumigating gases and other methods involving toxic materials and/or byproducts and can have adverse effects on perishable commodities.

A CPR can facilitate DBD surface plasma decontamination, which is rapid, e.g., taking only minutes for a 6-log reduction in viable levels of a multiplicity of human and plant pathogens. Unlike current procedures, including other plasma based methods for ozone production, surface plasma in accordance with the subject invention can be generated from ambient atmospheric air, such that no toxic materials are involved, and no high input of electricity or enriched gases is required. Since plasma is generated at atmospheric pressure and low temperatures, is non-corrosive and compatible with common environmental surfaces and delicate commodities, it can be used with surfaces and materials of different composition.

Embodiments of a Compact Plasma Reactor (CPR) can be incorporated into reusable fruit and vegetable shipping and storage containers, to harvest, transport, store, and distribute fruits and vegetables. Proper transport and handling of food is critical throughout the entire supply chain. Perishable products that require refrigeration have additional cost and traceability requirements. Handling issues can occur when produce experiences improper temperatures, such as during transportation delays due to weather, traffic, equipment or vehicle malfunction, or due to congestion at harbors, terminals, or when on loading docks or in warehouses. Imported products can wait days at the ports for testing, significantly reducing their shelf life.

Embodiments of the subject invention relate to a Compact Plasma Reactor (CPR) as small (~1 inch cube), having a modular self-contained battery powered unit designed to go inside a food container or "GreenBox" containing perishable produce to prevent or reduce losses due to spoilage. In addition to having a small size and minimal power requirements, advantages of the CPR include: no long-term toxic material used or produced, minimal carbon footprint, while utilizing a method for protecting perishable items from spoilage during retail/storage/shipping in a container using surface plasma generated by the CPR where one or more CPRs can be placed in the tote at the point of origin and recycled or disposed by the end user at retail.

Embodiment of the invention relate to a method and apparatus using the technical process of dielectric barrier discharge (DBD) surface plasma generation from ambient atmosphere for decontamination of air and surfaces within enclosed volumes. The primary application mode is for preservation of perishable commodities through reduction of surface spoilage organisms and destruction of evolved gaseous ethylene that causes premature ripening.

Embodiments of the present invention comprise a water treatment system based on an ozone producing Dielectric Barrier Discharge Plasma generator.

Herein PurplePure refers to the ozone producing, and initial mixing portion of the system (FIG. 25). Active Plasma Module (APM) refers to the Ozone generating portion of the PurplePure, consisting of circuitry and a replaceable DBD electrode. The device functions with an external flow or water pressure to the inlet.

Embodiments of the subject invention relate to an apparatus and method for treating water for drinking. In specific embodiments, the apparatus includes an ozone generator that generates ozone for mixture into the liquid, an AC to DC power supply, a venturi injector to mix the generated ozone and liquid, and a chamber into which ozonated water can be delivered where it reacts with and eliminates contaminates, and involves an end filtration step to remove remaining ozone and precipitated particulates. In further embodiments, a sedimentation filter is included in the water stream before the treatment system and an external water pump is included to introduce untreated source water to the system. A schematic of an embodiment of the system is shown in FIG. 25.

BRIEF DESCRIPTION OF DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DISCLOSURE

Figure 1:
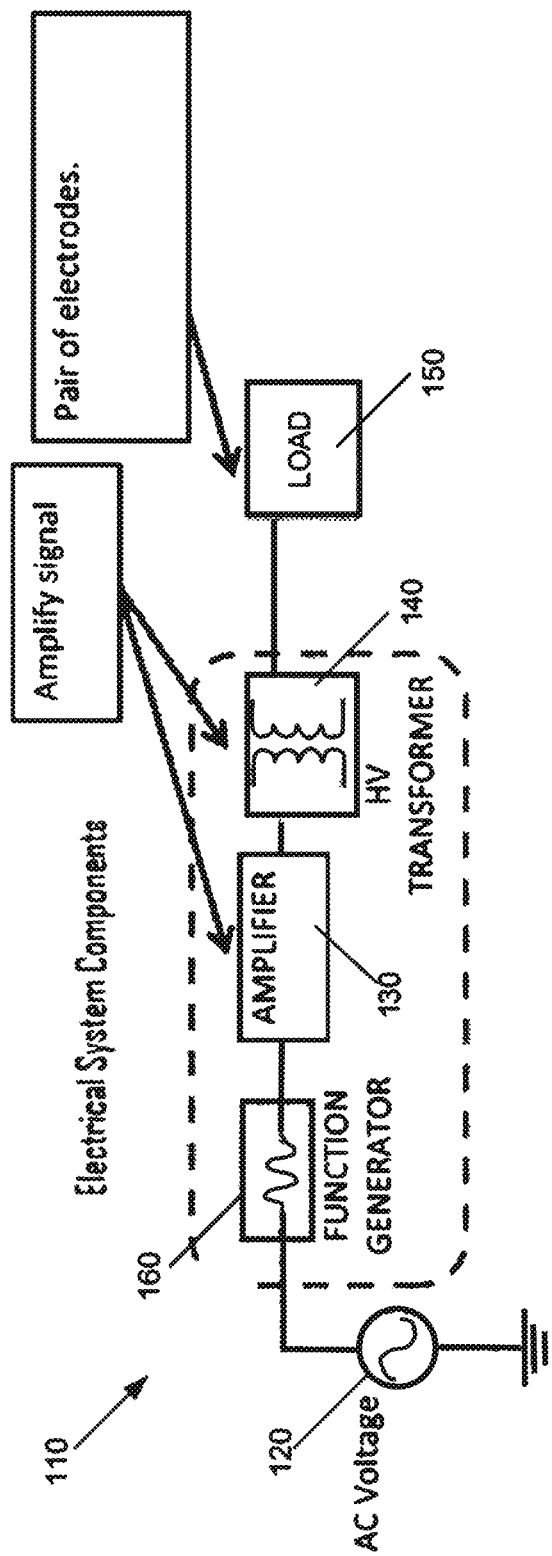
FIG. 1 is a schematic diagram of a plasma reactor system in accordance with an embodiment of the present disclosure.

Embodiments of the present disclosure relate to plasma reactor apparatuses, systems, and methods for providing power supply unit(s) for plasma generators. Power supply units of the present disclosure can be small and/or portable and can be used for a variety of applications. For example, power supply units of the present disclosure can be used to drive plasma generators having dielectric barrier discharge (DBD) devices, such as plasma actuators.

Power supply units of the present disclosure can provide power to at least one load. Each load can be, for example, an electrode, such as an electrode used for plasma generation. In an embodiment, a power supply unit can include a system which is capable of running more than one load. In an alternative embodiment, a power supply unit can include multiple systems put together and controlled by a controller. Each system can be, for example, a power amplifier such as a zero-voltage switching amplifier. The controller can be any controller known in the art capable of driving and/or switching voltage-providing systems, for example, a microcontroller or other circuit. In an embodiment, the controller can be a motherboard including a microcontroller and additional circuitry which can be provided to inhibit damage.

In an embodiment, a power supply unit can include a single power amplifier, which can be used to power on and off an array of loads, such as plasma generator(s). In an alternative embodiment, a power supply unit can include at least two power amplifiers controlled by a controller. The controller can be configured to turn on and off each power amplifier. The power supply unit can also include a switch connecting each load to a power amplifier. The controller can be configured to open and close the switches connecting the loads to the power amplifiers.

In one embodiment, the current and the voltage waveforms of the transistor provide a condition when the high current and the high voltage do not overlap simultaneously that minimizes the power dissipation and maximizes the power amplifier efficiency. Accordingly, an exemplary embodiment utilizes a power MOSFET transistor which has a built-in diode across its source and drain. This diode can inhibit reverse breakdown of the transistor and keep the power amplifier operational.

Embodiments of the subject invention can include any type of an over-current protection circuit that protects the circuit components of the power supply unit from damage in situations where the interaction between the load and the power amplifier yields high current levels that can otherwise damage the CPR device. This over-current protection circuit can also prevent the flow of current in the CPR circuit when a load is removed, until the load is replaced and the system is reset. The main reason for the increment of the CPR's current is the expected deterioration of the DBD electrode arrangement (load) that occurs after a considerable amount of use. Generally, the CPR's circuit operates at a steady current level, determined mainly by the load and operating frequency. However, after a considerable amount of use of the device, the dielectric material between the plasma electrodes can present signs of corrosion, yielding a progressive increase in current that can surpass the tolerance limit of the circuit or even cause the breakdown of the dielectric. Therefore, the CPR can incorporate a circuit that identifies the increase, or the increment, in the current and stops the operation of the circuit. The operation of the circuit can be reinitiated after the load (DBD electrode arrangement) is replaced.

Figure 23:
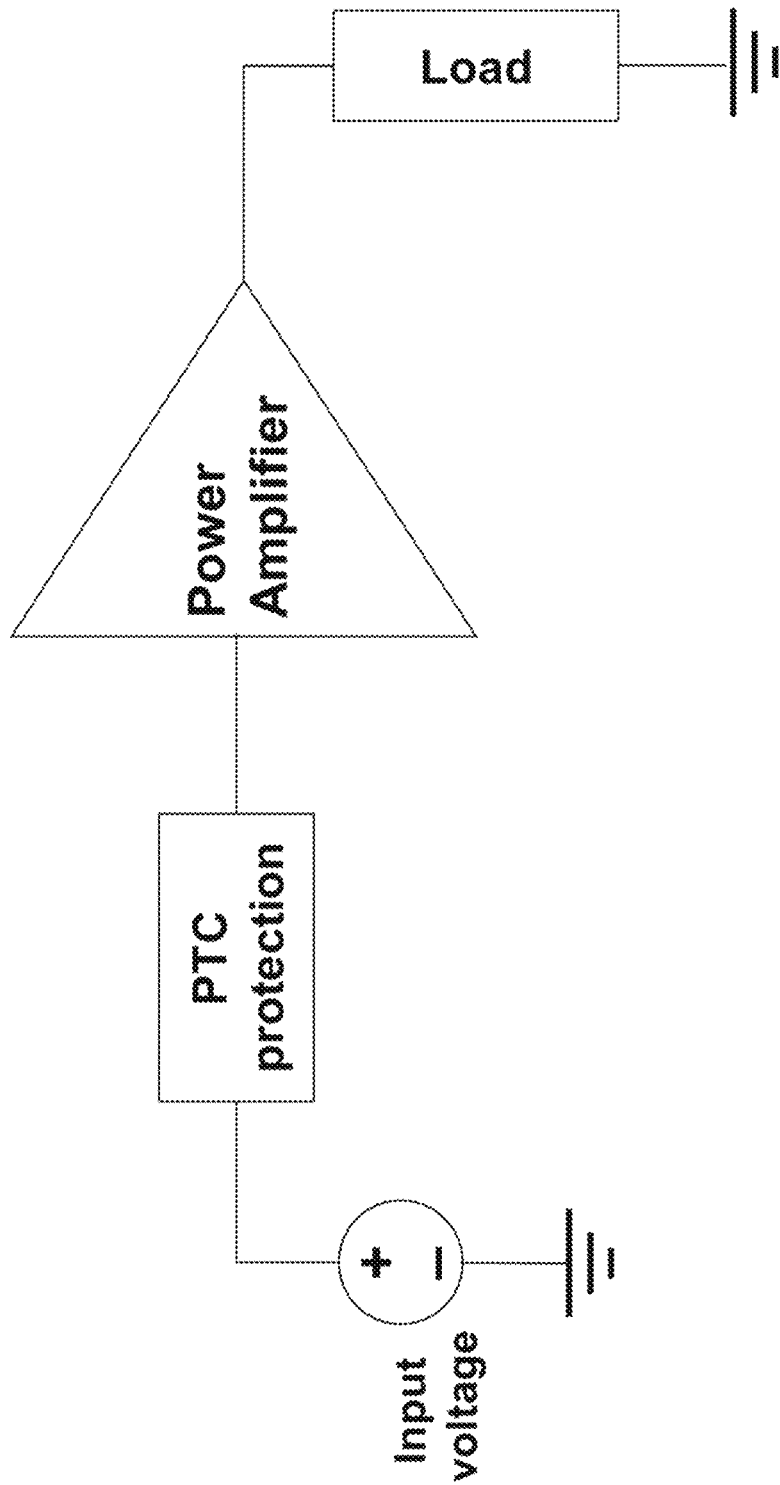
FIG. 23 shows a diagram of an embodiment of an over-current protection circuit in accordance with an embodiment of the invention.

Embodiments of the subject invention can incorporate a simple over-current protection circuit, such as the circuit shown in FIG. 23, where a Positive Temperature Coefficient (PTC) resettable fuse is connected between the DC input voltage and the rest of the CPR's circuit. The current rating of the PTC resettable fuse can be selected according to the desired operation of the CPR. After the load (e.g., the DBD electrode arrangement) is replaced, the device would be powered up again and the PTC would allow the flow of current and the subsequent generation of ozone.

Figure 24:
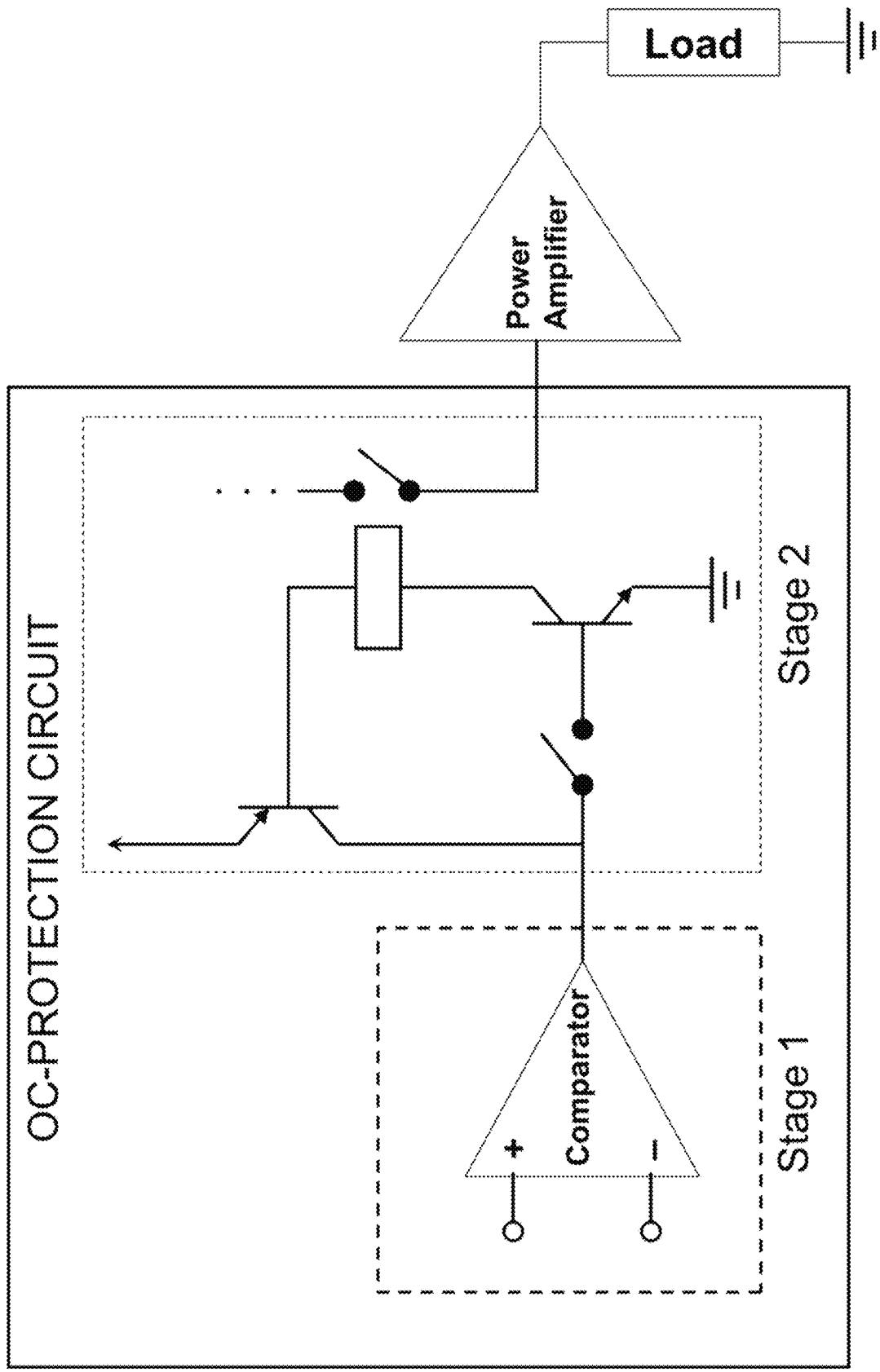
FIG. 24 shows a diagram of an embodiment of a power supply unit for driving electrodes of a plasma reactor in accordance with an embodiment of the invention.

In further embodiments, a more reliable alternative to the circuit in FIG. 23 can be used, such as a circuit that incorporates a more sophisticated module, which, in addition to stopping or limiting the flow of current, can also automatically disconnect the CPR from the DC power supply, allowing the replacement of the electrode arrangement (load) without electrical hazard. An example of such an alternative system is shown in FIG. 24. In this system the CPR circuit is divided in different stages. First, a comparator senses the change in DC current that is feeding the CPR's power amplifier. If the current increases beyond a certain threshold, the next stage of the OC-protection circuit is enabled and the current flow to the power amplifier is interrupted. Such stage includes a pair of complementary transistors and a relay switch. In order to protect the user when the load is being replaced, a manual switch is also added to the circuit so that the current does not flow back to the power amplifier circuit unless a manual switch is pressed.

The power supply unit of a plasma reactor system can also include a feedback mechanism, such as feedback circuitry, and the controller can be configured to control the feedback circuitry, which can be switched from load to load. The feedback circuitry can be configured to monitor the plasma reactor system, which can include monitoring the load(s), to determine if/when the value of a parameter of interest is outside an acceptable range and then adjust another parameter accordingly or to control operation of the plasma reactor system. For example, the feedback circuitry can be configured to control operation of the plasma reactor system, including activating or deactivating the power supply unit. Further, the feedback circuitry can be configured to adjust the frequency of operation based on, e.g., changes in the impedance of the load (or loads) of the power supply unit and/or changes in the voltage provided by the power supply unit. In many embodiments, the feedback circuitry can be configured to monitor (e.g., by measuring) an operational parameter.

A variety of sensor types can be employed as well with the feedback circuitry. The following are examples of sensors that could be used for sensing, feedback and control of the active surface or the plasma generator device itself: moisture/humidity sensors to detect moisture over the active surface or of the device or of a vehicle/structure to which the sensor is attached, air speed sensor to determine a speed of airflow over the active surface or of the device or of a vehicle/structure to which the sensor is attached, infrared beam to provide a curtain over the active surface or device; radio frequency field to provide a curtain over the active surface or device; motion sensor to detect movement over the active surface or of the device; acoustic beam to detect movement over the active surface or of the device; temperature sensors to determine contact by another object or change in the device; pressure sensors to determine contact by another person or object or change in the device, such as a foreign object (e.g., dust); capacitive sensors to determine contact by another person or object or change in the device; and conductivity sensors to determine contact by another person or object or change in the device.

As an example, a moisture sensor can be used to determine when adverse conditions (e.g., wet conditions) may be present for operation of a power supply unit and/or power amplifier, such as conditions making likelihood of a short-circuit failure possible.

Figure 18:
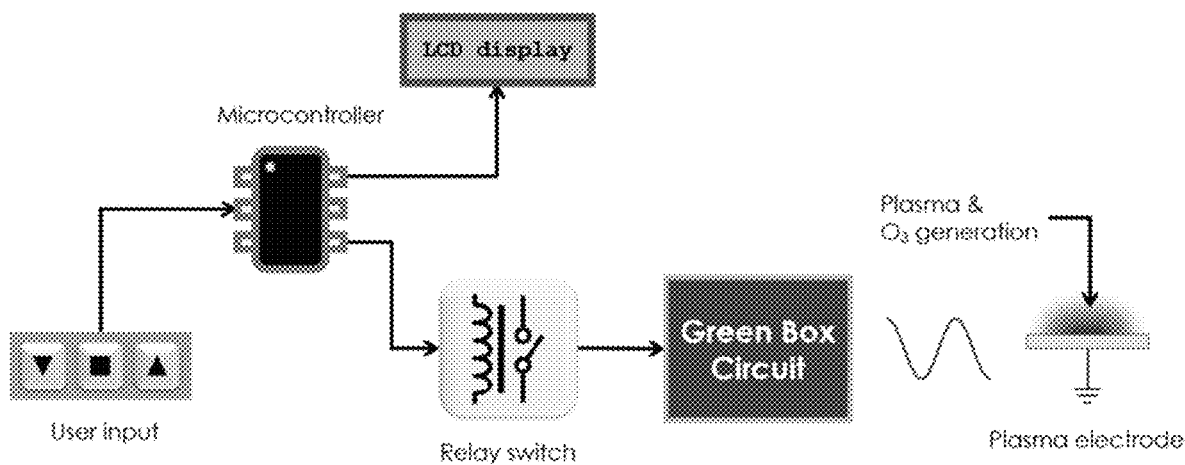
FIG. 18 shows a greenbox system diagram.
Figure 19:
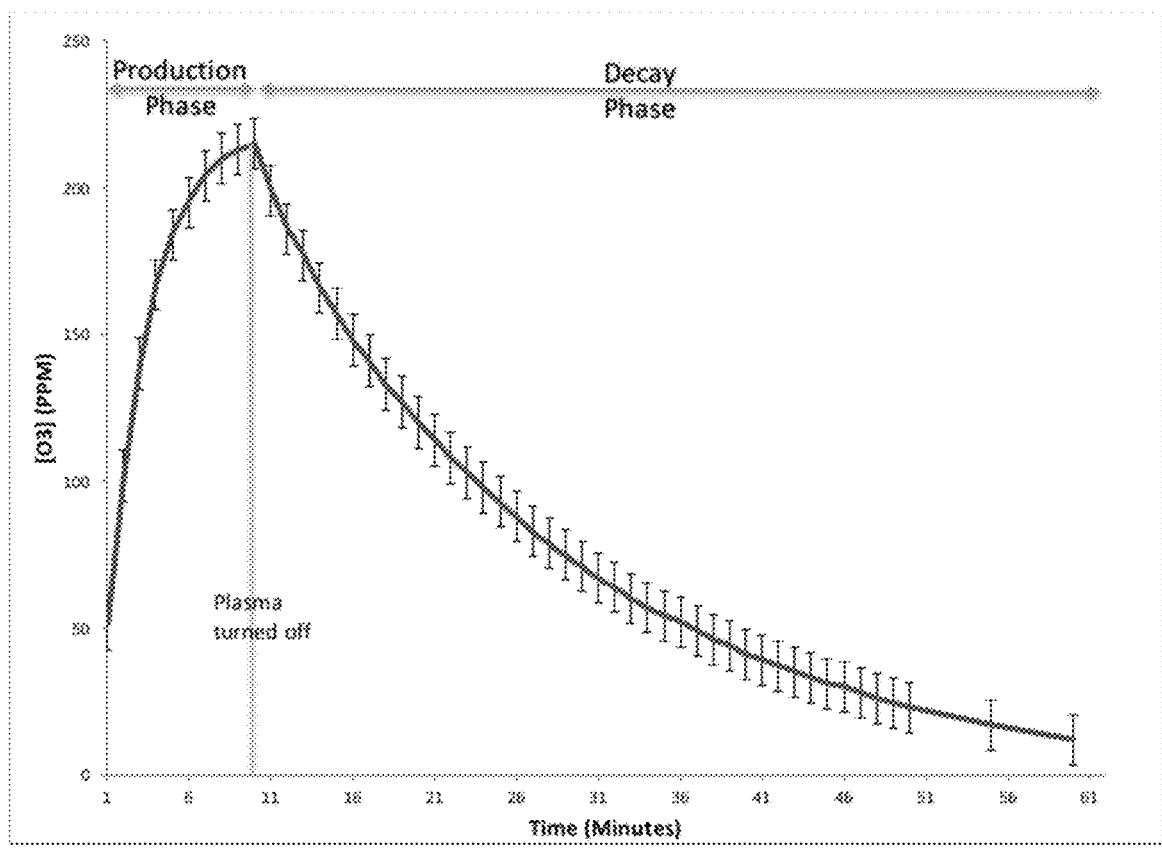
FIG. 19 shows ozone generation within a 3 cubic foot box.
Figure 20:
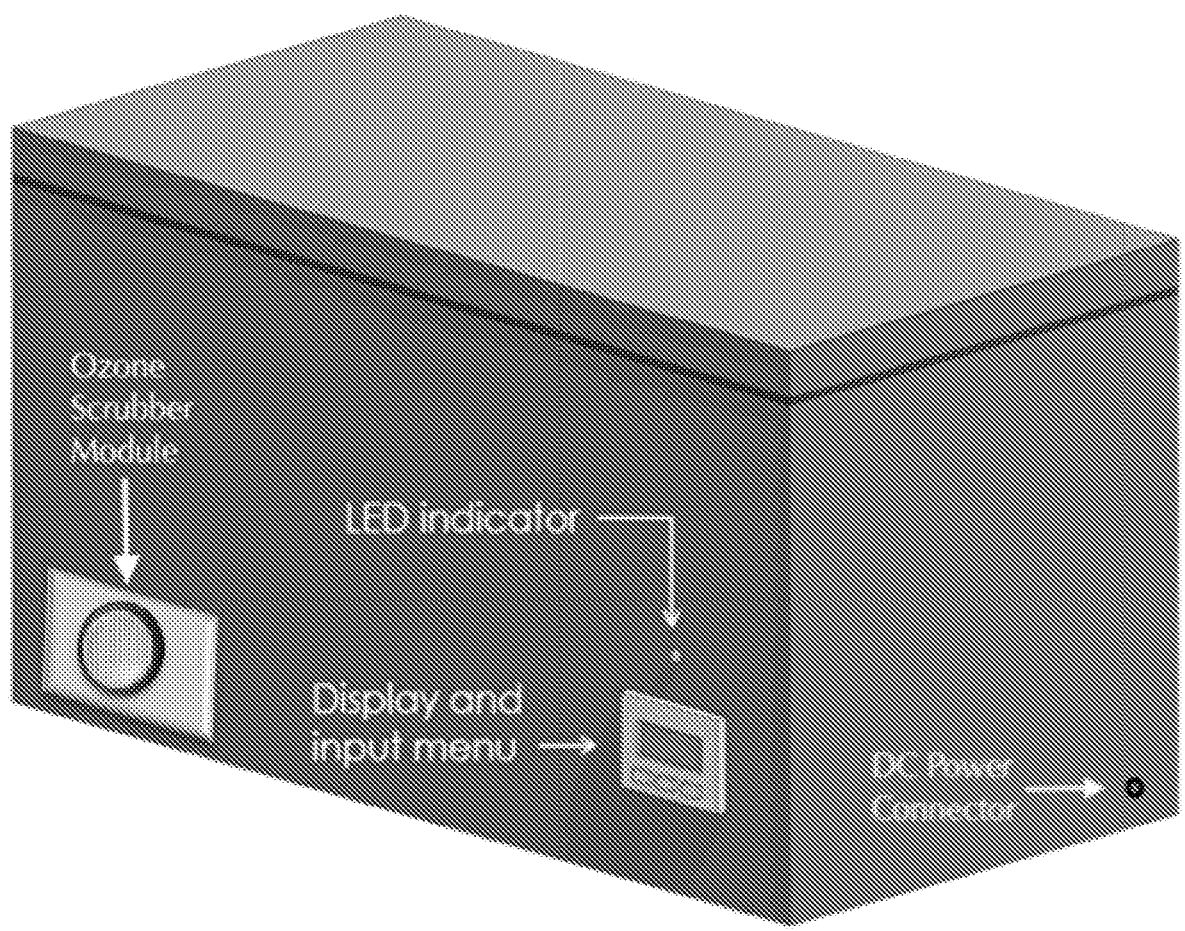
FIG. 20 shows an external view of the greenbox.
Figure 21:
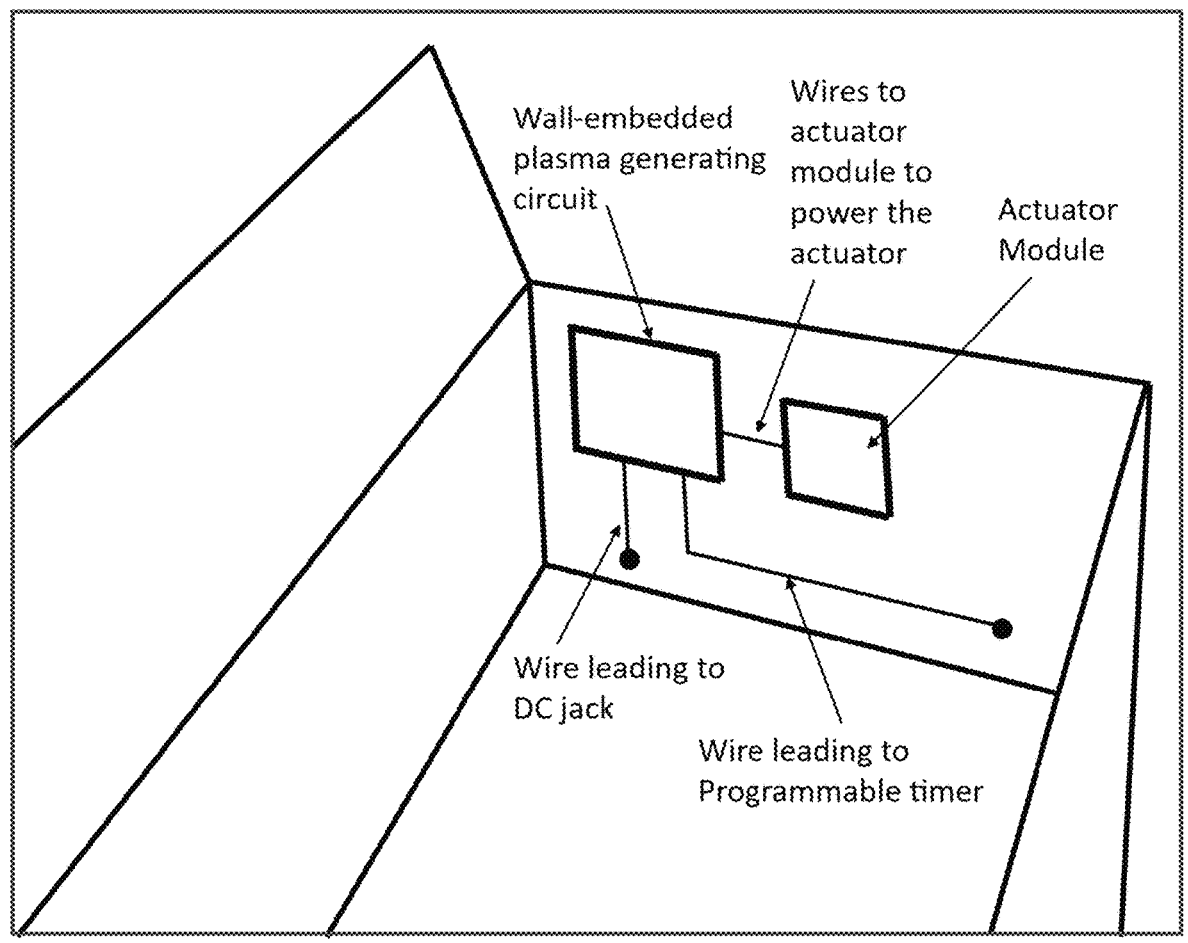
FIG. 21 shows an interior of the greenbox showing the actuator module and embedded circuitry.
Figure 22:
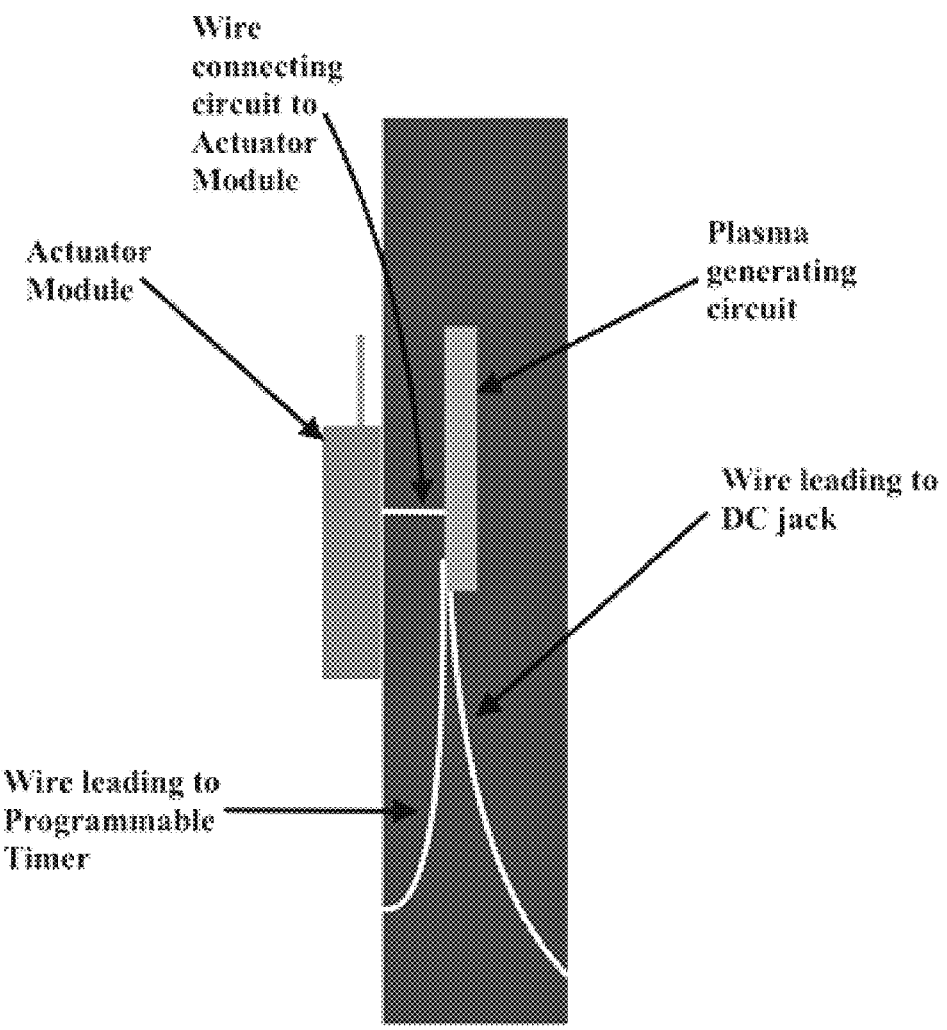
FIG. 22 shows a cross sectional view of the wall of the greenbox containing the embedded circuitry.

A timer module can be added to control the operation of the CPR. Instead of running continuously, the CPR can be programmed to operate at specific intervals and/or specific time of the day/night. In an embodiment, this timer module increases the lifespan of the CPR system, reduces energy consumption, and regulates ozone to safe levels. The basic principle of operation of a timer module in accordance with an embodiment of the invention is illustrated in FIG. 18. In this schematic, the timer function is performed through a dedicated integrated circuit (IC) chip such as a microcontroller. In alternative embodiments, a simpler timer IC or unit can be utilized. First, preset parameters of time are selected through a mechanical input interface, such as one or more buttons, a touch-screen display, etc. This input via the interface is converted to electrical signals that travel to the input ports of the microcontroller enabling the timer registries of the microcontroller. When the programmed time equals the time tracked by the microcontroller's inbuilt clock, an output of the microcontroller can be enabled, allowing the current flow in the coil of a normally open (NO) relay switch. The switch of the relay is placed at the input branch of the CPR's power amplifier. Since the switch is normally open, the CPR only works during the time period the microcontroller enables the output associated with the relay. In addition, an LED can be added to serve as an indication that the CPR is in operation.

The same microcontroller added to the embodiment of the subject CPR to realize the timer functions can be connected to the sensors that measure temperature, humidity, movement, etc., to monitor such parameters and turn the power of the unit on and off.

In some portable versions of the embodiments of the subject CPR the DC power required to activate the device is provided by batteries.

Versions of the embodiment of the subject CPR includes the conversion of the AC power provided by the electrical grid (wall outlet) to suitable DC power levels required to activate the device. Accordingly, this embodiment does not need an external DC power supply, but, instead, can be connected directly to the electrical grid.

In many embodiments, a power supply unit can provide voltage to at least two loads. Each load can be, for example, an electrode, such as an electrode used for plasma generation. In many embodiments, a power supply unit can include an inductor and/or capacitor. For example, the power supply unit can include one or more power amplifiers, and each power amplifier can include one or more inductors and/or capacitors. In one embodiment, the load can include dielectric barrier discharge (DBD), where a first electrode, or set of electrodes, is exposed at the surface to the surrounding atmosphere (or covered with a coating) and a second electrode, or set of electrodes, is embedded inside a layer of insulator. A voltage can be applied between the first electrode, or set of electrodes, and the second electrode, or set of electrodes, to create a plasma at the surface. In order to disperse the plasma in a continuous fashion over the surface phase lagged electrode circuitry may be employed. In one embodiment, the phase lagged electrode circuitry applies voltages across corresponding electrodes from the first set of electrodes and the second set of electrodes, which form electrode pairs, such that different electrode pairs are excited with voltages having a phase lag compared with the voltage applied to the adjacent electrode pair. In an embodiment, the electrode spacing in each direction is such that the discharge is on both sides of the electrode. One set of electrodes may be powered with a pulsing AC or DC voltage and the other electrode set can be grounded. For AC voltage various waveforms can be utilized, such as sinusoidal, ramp, and sawtooth waveforms. The electrodes may also be operated at a beat frequency. In addition, application of fixed potential (DC) can be implemented. The electrode spacing may vary from, for example, a few microns to several millimeters.

In certain embodiments, the voltage potential applied to a power supply unit can be applied in a duty cycle. A duty cycle can advantageously minimize the power requirement. In each cycle of the duty cycle, the voltage potential can be applied to a system of the power supply unit for one or more portions of the cycle and not applied to that system for the other portions of the cycle. During such other portions of the cycle, the voltage potential can be applied to another system of the power supply unit or not applied to the power supply unit at all. In an embodiment, the voltage potential can be applied as a repeating cycle of one or more pulses. For example, a power supply unit can include three systems each providing power to a load, for a total of three loads. A voltage potential can be applied to each system of the power supply unit for one third (33.3%) of the cycle duration, in one embodiment.

Embodiments of the present disclosure provide power supply units that are portable and that can provide voltages in the kV range, which can, e.g., produce DBD plasma. In a specific embodiment, the power supply unit can provide voltages of at least 6 kVpp. In addition, power supply units of the present disclosure can power more than one load. For example, a power supply unit can generate plasma on more than one load. Each load can be, for example, an electrode. For example, the power supply unit can either include a single system capable of running more than one load or include multiple systems, each simple and small enough so multiple systems can be put together. In the case of multiple systems, the multiple systems can be controlled by a controller. The loads can produce plasma simultaneously and/or a duty cycle can be applied. The number of loads will vary depending on, for example, the desired application and/or the desired surface area to cover.

Referring to FIG. 1, in an embodiment, a power supply 110 can include a power input supply 120 and a power amplifier including an amplifier 130 and a transformer 140. The power supply unit 110 can be connected to multiple loads 150, such as two electrodes forming a plasma generator. The load can have, for example, a size of 1.5 inches by 1.5 inches, as a non-limiting illustration. The power input supply 120 can operate with a DC input signal and output an AC signal with frequencies of the order ~kHz, in some embodiments. Further, in some embodiments, the power input supply 120 can operate with an alternating input signal, such as, in conjunction with, a function generator 160.

In an embodiment, a power supply unit 110 can include at least one system having a circuit topology including a transistor 210 (FIG. 2), an inductor 220 (FIG. 2), a capacitor 230 (FIG. 2), and a transformer 140. The transistor can be used as a switch. Such a system is an amplifier or power inverter, and this amplifier is a zero-voltage switching (ZVS) amplifier, which yields 100% efficiency theoretically.

Figure 2:
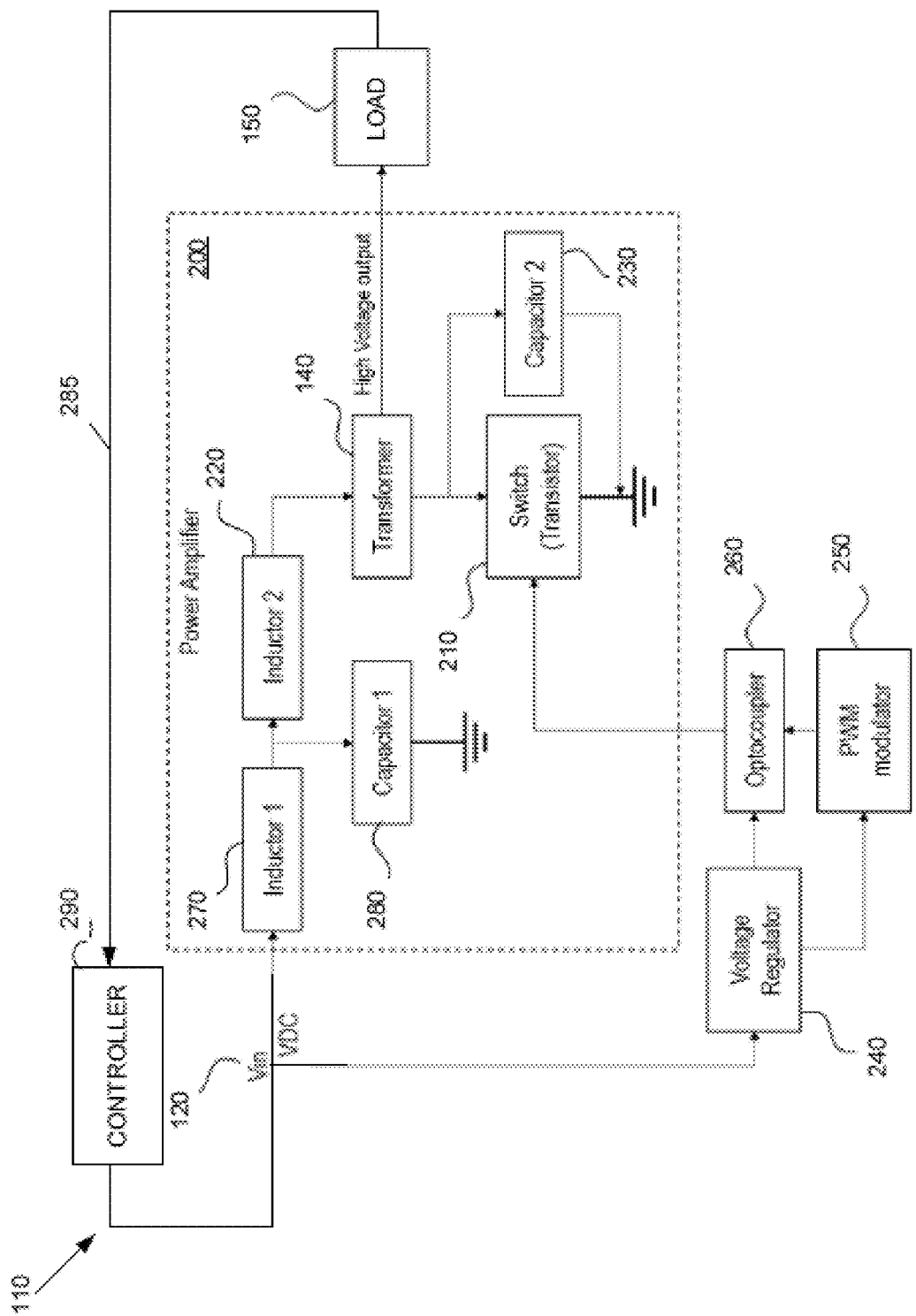
FIG. 2 is a schematic diagram of components of a power supply unit of the plasma reactor system of FIG. 1 in accordance with an embodiment of the present disclosure.
Figure 3:
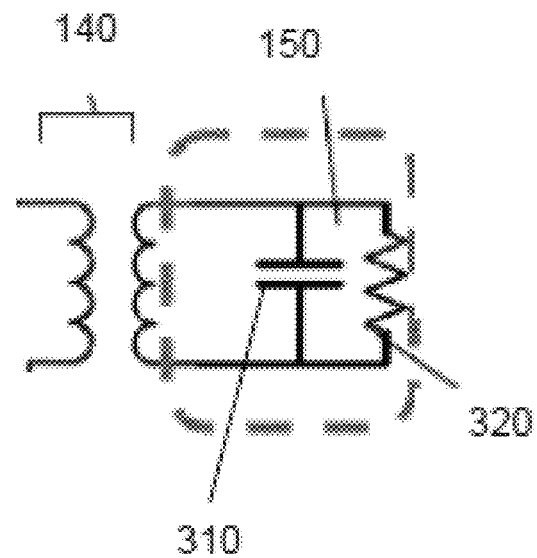
FIG. 3 is a circuit diagram representation of a load of a plasma reactor system in accordance with an embodiment of the present disclosure.

Referring to FIG. 2, the transistor or switch 210, inductor 220, capacitor 230, and transformer 140 can be arranged as depicted, in one embodiment. The load 150, such as an electrode, can be represented by a capacitor 310 and a resistor 320 in parallel, though embodiments of the present disclosure are not limited thereto, as represented in FIG. 3. The load 150 can be connected to the secondary side of the transformer 140 (i.e., the other side from which the power input supply 120 system is connected). The impedance across a wide range of frequencies looking into the primary side of the transformer 140 can be measured.

The self-resonance frequency of the transformer 140 and the load 150 can then be selected for various embodiments and/or applications. This can yield maximum voltage amplitude on the load 150 because maximum real impedance is seen on the primary side of the transformer 140. The capacitor 230 (across the drain and the source of the transistor 210) can be a component with respect to allowing proper zero-voltage switching (ZVS) operation to be obtained and yielding a high efficiency. In certain embodiments, the frequency of the transformer 140 and the load 150 can be selected or tuned to work at a different frequency parameter or range, which allows for adaptation of the power supply unit 110 for many different applications. Accordingly, capacitive values of the power amplifier 200 may be tuned to adjust for modified frequency values to match the impedance of the load 150. Thus, the capacitor 230 comprises of a variable capacitor, such as a capacitor matrix component, or a diode with voltage-controlled capacitance, known as varactor, in some embodiments. Further, in some embodiments, the power input supply 120 comprises a variable frequency generator.

Referring back to FIG. 2, the switch 210, in one embodiment, requires lower voltage than other components, such as the transformer 140. Accordingly, voltage regulator 240, pulse width modulator 250, and optocoupler 260 circuitry components are provided to produce a low voltage square wave to drive the switch 210, in one embodiment.

In certain embodiments, a low-pass filter is included, because the current across the inductor 220 and the transformer 140 can oscillate, which can lead to a negative current fed back to the power input supply 120. Thus, the low-pass filter block this returning current and only allows DC current and DC voltage being drawn from the power input supply 120. Accordingly, in one embodiment, the power supply filter includes an inductor 270 and a capacitor 280, as shown in FIG. 2.

Embodiments of the power supply units 110 in accordance with the present disclosure can achieve advantageous results compared to existing amplifiers. Typically, a full bridge rectifier is only practical for a single load system. According to embodiments of the present disclosure, a power supply unit 110 can include multiple amplifiers (systems) and multiple loads and can have a simple topology with a small number of components and small size. Also, the shunt capacitance included in designs of the present disclosure increases efficiency by helping to obtain ZVS operation. Power supply units of the present disclosure can advantageously obtain kV-level output voltages with high efficiency. In accordance with the present disclosure, power supply units advantageously achieve high efficiency with small size and simple topology, thereby allowing multiple power amplifiers (systems) and multiple loads.

Figure 4:
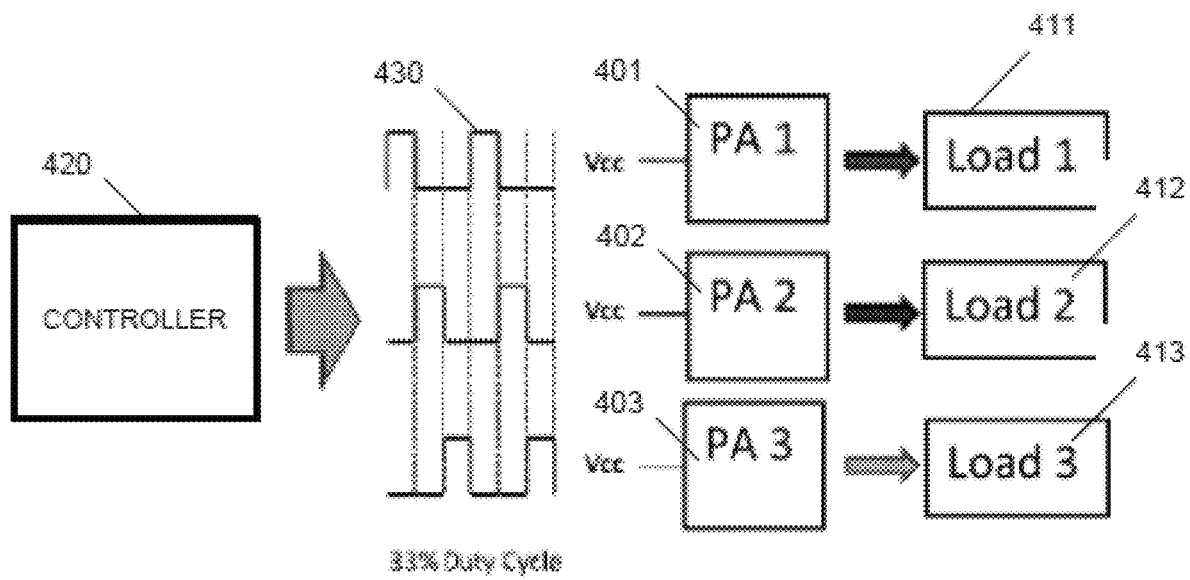
FIG. 4 is a schematic diagram of a power supply unit having multiple loads controlled by a controller in accordance with an embodiment of the present disclosure.

In addition, embodiments of the present disclosure are advantageously capable of running multiple loads. Small and simple systems can be used that can be scaled up easily. Referring to FIG. 4, a power supply unit can include multiple power amplifiers systems 401, 402, 403 each aiding in powering a load 411, 412, 413, in one embodiment. The systems, or power amplifiers (PAs), can be controlled by a controller 420. Though FIG. 4 shows three power amplifier systems 401, 402, 403 and three loads 411, 412, 413, embodiments of the present disclosure are not limited thereto.

As discussed, duty cycling can be used for applying power to the PAs 401, 402, 403. In an embodiment, the signal 430 applied to the PAs 401, 402, 403 can be applied to each PA for a portion of the cycle. For example, a power supply unit can include 3 PAs each powering a load, and each PA can have a signal applied to it for one third of the cycle, as shown by way of example only in FIG. 4. In certain embodiments, the controller 420 can control the application of the signal to the PAs.

Referring back to FIG. 2, a main feature of an exemplary embodiment of the power supply unit 110 is the switching power amplifier that is configured to set up and convert that step up and convert low DC input voltage into a very high AC voltage (kilovolts range), in which the power amplifier 200 utilizes the transistor 210 as a switch. To control the switching frequency and hence the output voltage frequency, a pulse width modulator (PWM) 3 with a 50% duty cycle is utilized in one embodiment. To guarantee appropriate functioning of the PWM circuit 3, a voltage regulator 2 is utilized along with an optocoupler 4 to protect circuitry components from voltage spikes coming from the output during plasma generation by the load 150. A circuit of the power supply unit 110 can include a feedback portion or mechanism 285 that feeds a controller 290, in one embodiment, as previously discussed.

In accordance with an embodiment of the present disclosure, a working frequency of the power supply unit 110 is set to match the resonance frequency of the transformer 140 attached to the load 150. By eliminating the reactance, the power transfer to the load 150 is increased and this, at the same time, has the advantage that the transformer 140 and load 150 can be considered as a resistor and the entire circuit can be reinterpreted as an RLC circuit.

In determining values of circuit parameters at resonance, two differential equations are yielded, as understood by one of ordinary skill in the art. One for when the switch 210 is on and one for when the switch 210 is off. In the ideal scenario, the switch 210 would have an instant transition from short to open (or vice versa) with no loss in power. However, in reality, there is still current passing through the switch 210 in the transition from short to open, and there is still voltage in the switch (transistor) 210 from open to short.

Therefore, to minimize the power loss during these instances, the drain voltage of the switch 210 and its derivative needs to be as close as zero as possible, which is referred to as zero voltage switching condition (ZVS). By numerically solving the two differential equations (see Appendix) and calculating the appropriate value for inductors 220, 270 and for the capacitor 230, the ZVS condition can be satisfied. Moreover, by the capacitor 230 comprising a capacitor matrix component, or other type of variable capacitor, that can be engaged to a desired capacitance value, the capacitance parameter can be adjusted to account for a changing operating frequency and to provide a matching impedance with the load 150.

It is noted that, while operating at the resonance frequency, the values of the inductors 220, 270, and the capacitor 230 can be set to have maximum power transfer by achieving zero voltage switch conditions when the switch 210 switches on and off. In particular, the capacitor and inductor values can be determined specifically for the resonance frequency. However, if the load 150 changes, then the resonance frequency also changes. Therefore, using a capacitor matrix as capacitor 230, the capacitance value of the RLC circuit can be tuned or adapted to any changing conditions of frequency or impedance. In particular, impedance matching on a primary side of the transformer 140 may be performed using a variable capacitor 230 (e.g., capacitor matrix component) to account for an impedance change at the load 150, in one embodiment.

Figure 5:
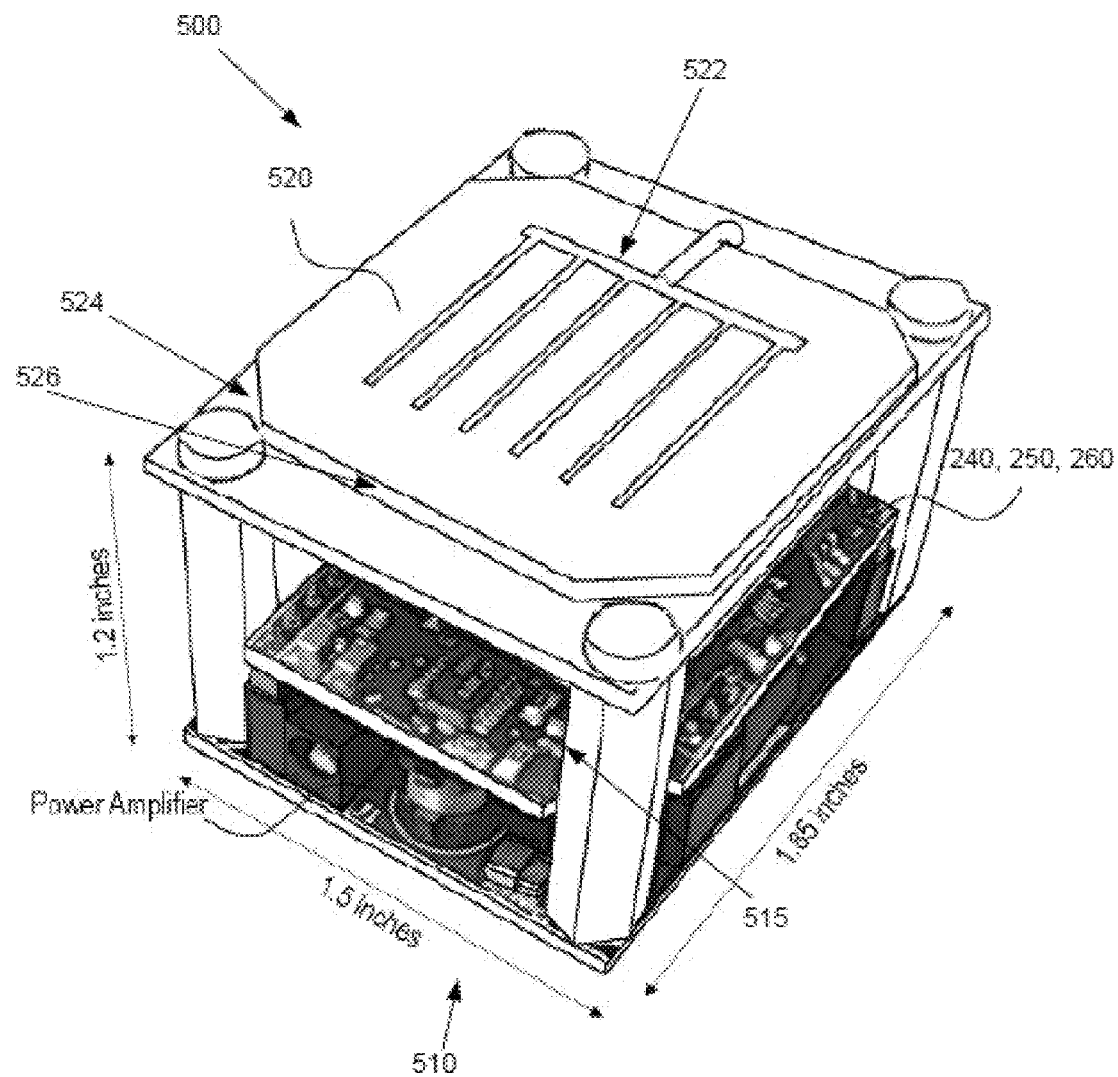
FIGS. 5-7 are diagrams of an embodiment of a structural arrangement of various components of a plasma reactor device or system in accordance with the present disclosure.

Next, FIG. 5 shows an embodiment of a structural arrangement of various components of a plasma reactor device 500 comprising the power amplifier circuit 510, switching power unit 515 (e.g., voltage regulator 240, pulse width modulator 250, and optocoupler 260), and a plasma generator load 520 in accordance with the present disclosure. In an exemplary embodiment, printed circuit boards (PCB) may be made of a common dielectric substrate material such as FR4 material with copper conductive layers, while the plasma generator load 520 may have any general shape, such as square shape, and is composed by two metal electrodes separated by dielectric material.

In the figure, the upper electrode 522 is a positive electrode and has a comb shape. The bottom electrode 524 is negative and has a square shape. The geometrical shape of both electrodes can change for different embodiments and for different applications. Electrodes 522 and 524 are separated by a dielectric material 526 that can have different thicknesses and can be made of different materials such as glass, ceramic substrates, PTFE (Teflon), liquid crystalline polymer and composites such as Teflon-ceramic, hydrocarbon-ceramic, etc., for various embodiments. The substrate can also be made of flexible material. Under the negative electrode 524, another layer of dielectric material may be added in various embodiments.

Figure 12:
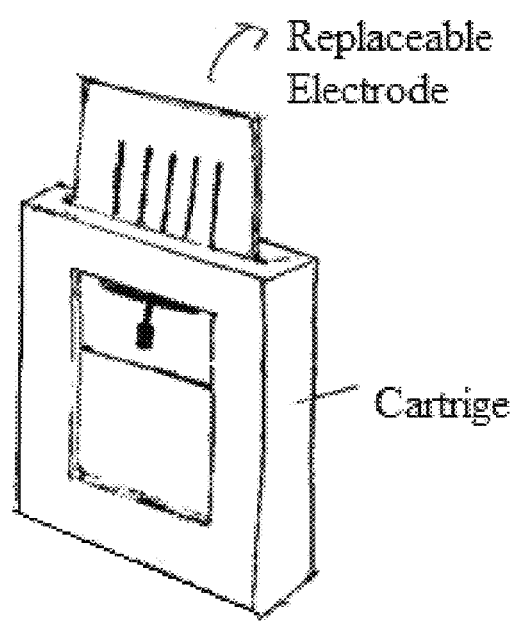
FIG. 12 shows the example of the CPR's electrode configured as a replaceable cartridge.
Figure 13:
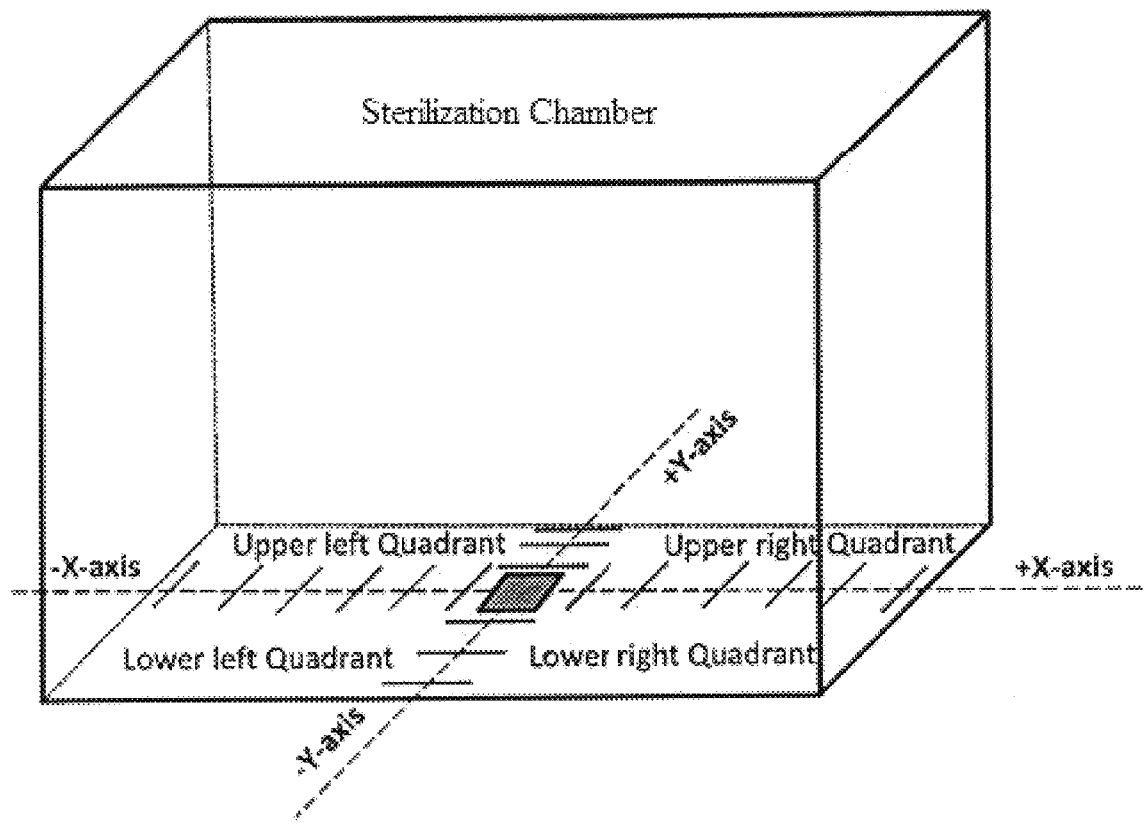
FIG. 13 shows a Sterilization chamber Test Volume Enclosure used to demonstrate rapid equilibration of ozone levels by virtue of APM flow actuator function that induces a three-dimensional body force to mix ozone with surrounding air for rapid mixing and equalization of ozone levels within the container.
Figure 14:
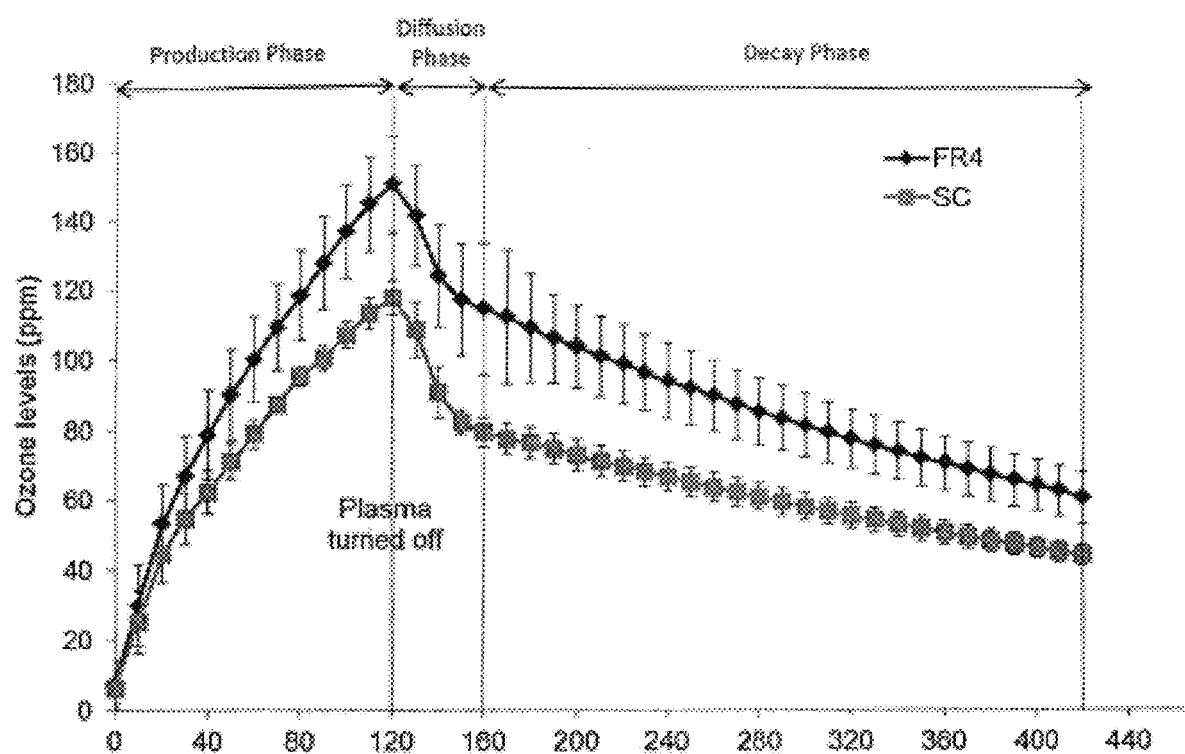
FIG. 14 shows the time course and concentration of ozone generation within a volume enclosure during and after a 2-minute activation of the APM device.

An embodiment of the CPR device may include a replaceable cartridge system that allows the easy replacement of the DBD electrode arrangement, such as when the dielectric material experiences excessive wear and corrosion. An example of such system is shown in FIG. 12. This system is designed to work in conjunction with the over-current protection circuitry (such as shown in FIGS. 23 and 24) to avoid danger of electric shock. The cartridge receptacle (labeled cartridge in FIG. 12) is made of a non-conductive material, and has two flexible metal contacts that coincide with the position of the ground and high-voltage pads of the DBD electrodes (load). When the replaceable electrode cartridge (labeled replaceable electrode in FIG. 12) is inserted current flows to the electrodes through the metal contacts of the cartridge receptacle.

The plasma generator load 520 is not limited to the particular pattern or style shown in FIG. 5. For example, many types of plasma actuators can be used for various types of applications. Possible applications include flow control (e.g., to reduce drag), deodorization, surface decontamination, sterilization, ozone gas production, etc. Accordingly, electrodes can be designed for a specific application and the power supply unit 110 and related components are configured to be tuned or adjusted to provide for optimum operating performance for the desired application. Thus, with reference to FIG. 5, the top reactor or load plate of the plasma generator load 520 can be switched with another plate design while still using the same power supply components, in accordance with the present disclosure.

Figure 11:
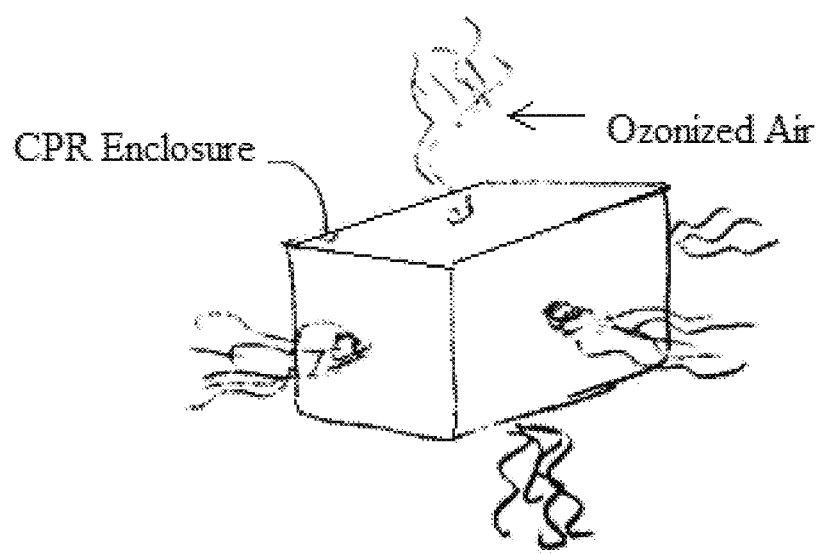
FIG. 11 shows the example of an enclosure with holes/openings containing the CPR. The ozone produced by the CPR is ejected through the holes.

The DBD electrode arrangement can induce air flow depending on the geometry/shape of the electrode among other factors. This air flow can be used in several ways to modify and/or enhanced ozone distribution. For example, the CPR can be placed in a small enclosure where the ozonized air is ejected through different holes/openings to improve the ozone distribution. The ozone can be ejected by the action of the hydrodynamic force induced by the plasma electrode or by a miniature fan system that could also serve as a coolant. An example is shown in FIG. 11, where the enclosure has one or more openings connecting an interior of the enclosure to an exterior of the enclosure.

Figure 6:
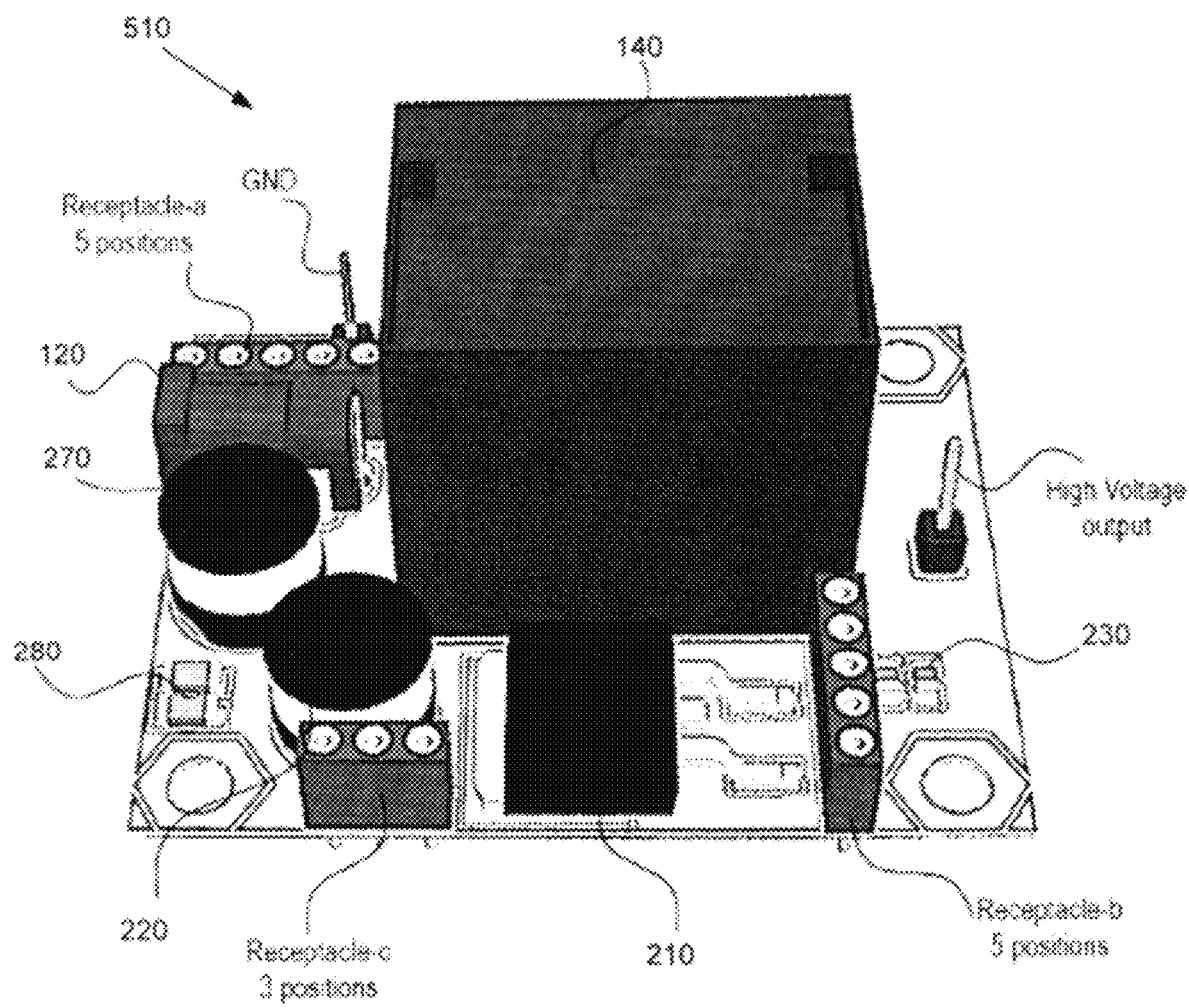
Figure 7:
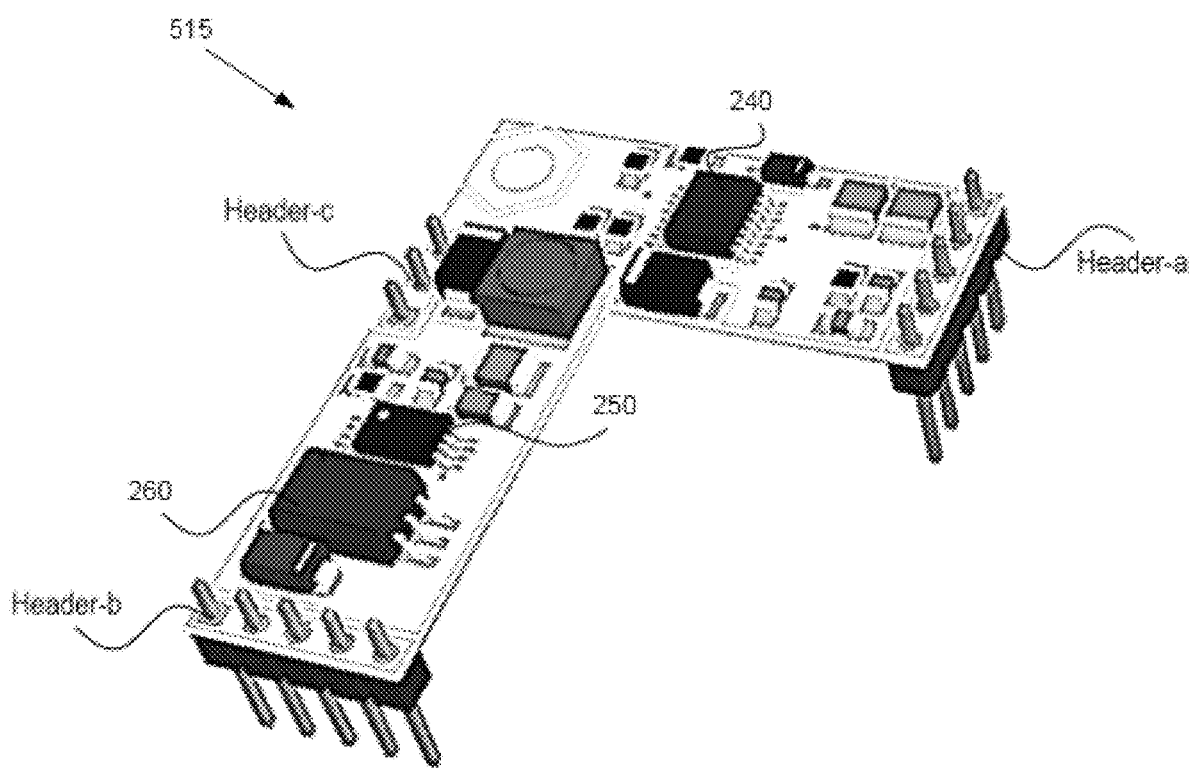
Figure 8:
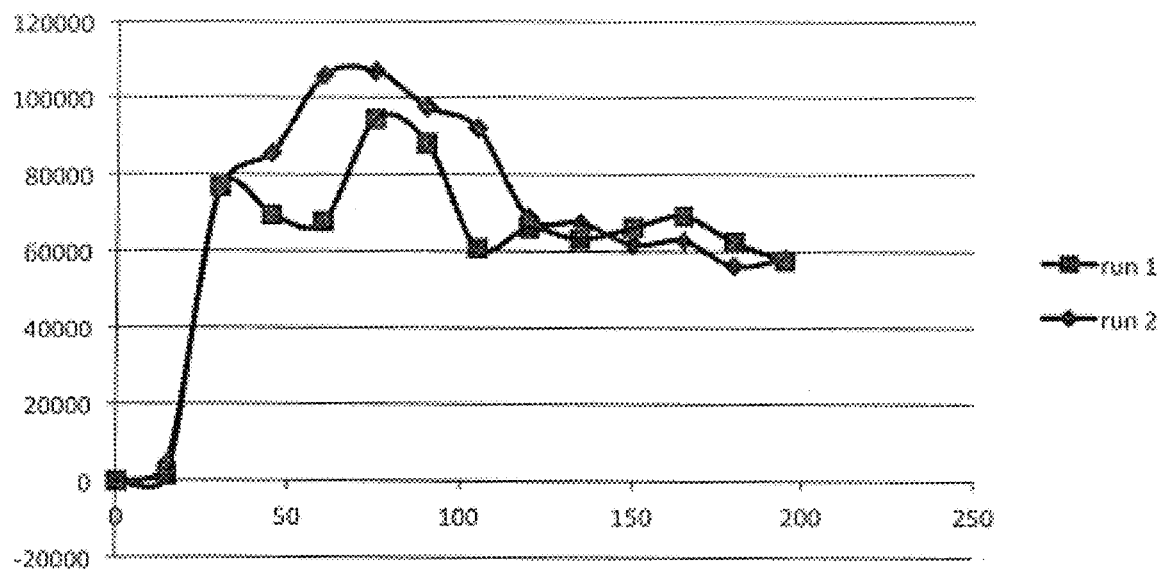
FIG. 8 shows ozone generation data in a 2'×2'×4' chamber, where the horizontal axis is time in seconds and the vertical axis is ozone concentration in ppb, for an input voltage of 20 volts.
Figure 9:
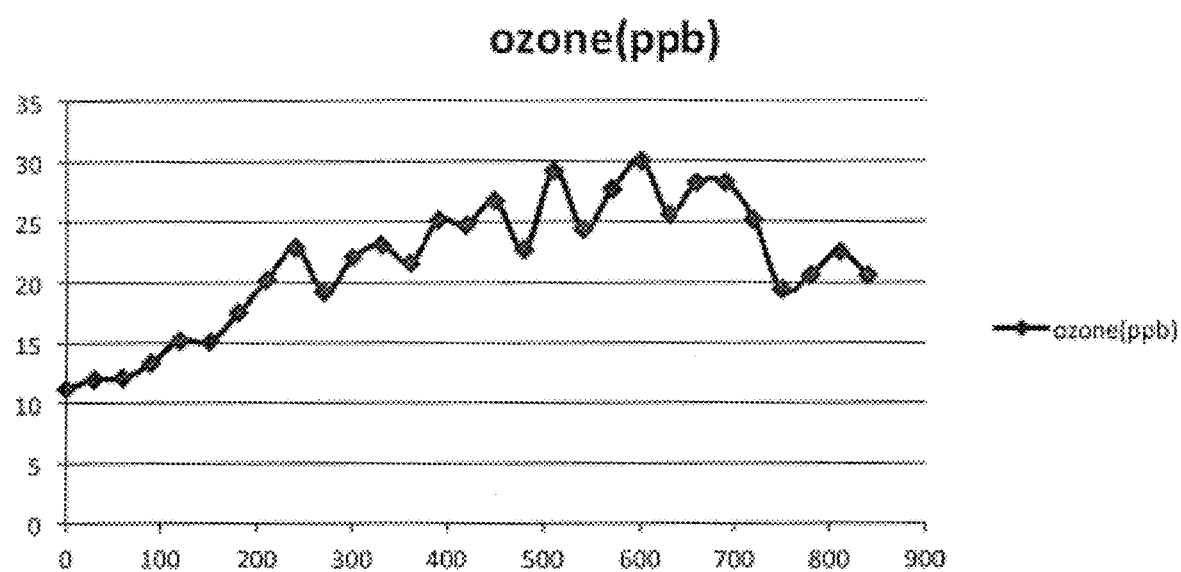
FIG. 9 shows ozone generation data in a 20'×15'×10' room, where the horizontal axis is time in seconds and the vertical axis is ozone concentration in ppb for an input voltage of 20 volts. The measurement was done at 20 inches (508 mm) from the plasma reactor.

Referring now to FIGS. 5, 6, and 7, components of the power reactor unit 500 are shown integrated in, but not limited to, a vertically-stacked arrangement. In particular, voltage regulator 240, pulse width modulator 250, and optocoupler 260 are shown built on a thin L-shape circuit board 515 held in a substantially level position elevated above the power amplifier circuit 510 (built on a thin printed circuit board). In this non-limiting example, the L-shape board has three headers strategically located, namely header-a, header-b, and header-c, as shown in FIG. 7. Each of these headers is attached to the receptacles on power amplifier circuit 510 of FIG. 6, namely receptacle-a, receptacle-b and receptacle-c, in the vertically-stacked arrangement.

Stated dimensions for the plasma reactor device in FIG. 5 indicate that the unit is 1.2 inches×1.5 inches×1.85 inches in this exemplary arrangement. However, other sizes—both smaller and larger—are possible in different embodiments. Further, in some embodiments, the respective components may be contained or integrated in a single flat planar layer and/or may be distributed in separate layers (e.g., circuit boards) having different geometries.

Figure 10:
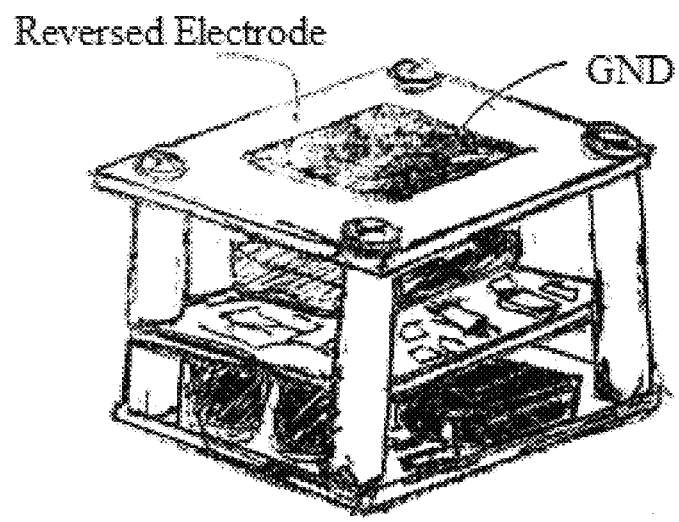
FIG. 10 shows an embodiment of the CPR, where the electrode arrangement has been positioned in a reverse fashion; i.e., the ground electrode is exposed and the high voltage electrode is looking towards the circuit.

In the stack arrangement of the CRP the electrode can be placed in a reverse fashion (looking towards the circuit), as shown in FIG. 10. This arrangement can serve different purposes. For example, if it is desired to avoid the ozone rapidly spreading in a single direction due the hydrodynamic force induced by the plasma, and, instead, it is desired for the ozone to slowly distribute in a more isometric fashion, the arrangement shown in FIG. 10 can be used. Also, the stacked configuration can be useful to avoid exposure of the high-voltage electrode for safety concerns.

Heat dissipation from components such as one or more transformers, one or more inductors, and/or one or more transistors can tend to increase the average temperature of the circuit, where it is desirable for the temperature to remain below the rating of the electronic components, to avoid limiting the lifespan of the device. Moreover, hot temperatures should be avoided when adapting the circuit to certain applications. Therefore, the CPR circuitry can be designed to include cooling systems/materials in trouble areas. In addition, a miniature fan system can act as a coolant and serve to eject the ozone in the manner described with respect to FIG. 12.

In accordance with the present disclosure, an exemplary embodiment a plasma reactor device is capable of generating dielectric barrier discharge plasma and consequently ozone with very low power and very compact size (less than 50 cubic centimeters). For example, the plasma reactor device is portable and able to operate with batteries. The device includes a power amplifier that converts a low DC input voltage into a very high AC output voltage and that also requires, pulse with modulator an optocoupler, and a voltage regulator. In one embodiment, a plasma reactor load with electrodes separated by a ceramic substrate is connected to an output. Such a scalable plasma reactor device is useful for a range of portable applications, including air flow control, sanitizing vacuum cleaner, deodorizer, etc., that can benefit from its low power consumption and small size. For further details and information on power supply units and plasma generators/actuators, see U.S. 2014/0346875 publication, titled "Method and Apparatus for Providing Power."

Data for Ozone Generation

| time (s) | run 1 | run 2 | run 3 | run 4 | run 5 | in ppb |
|---|---|---|---|---|---|---|
| 0 | 17.9 | 19.8 | 19.3 | 19.5 | 19.4 | |
| 15 | 1485.3 | 4717.8 | 22.3 | 21.5 | 22.8 | |
| 30 | 76845 | 76372.9 | 22 | 20 | 23.5 | |
| 45 | 69413.3 | 85604.8 | 20 | 20.6 | 5630.4 | |
| 60 | 67730.3 | 105758 | 21 | 18.8 | 5910.3 | |
| 75 | 94338 | 106811.8 | 42.1 | 35.8 | 6266.6 | |
| 90 | 88012.7 | 97457.8 | 390.6 | 327.5 | 7427.7 | |
| 105 | 60790.3 | 91901.4 | 777.4 | 688.1 | 7817.2 | |
| 120 | 66078.2 | 68844.4 | 960.9 | 1800.2 | 8828.4 | |
| 135 | 63205.6 | 67412.7 | 2489.1 | 3333.5 | 9009.7 | |
| 150 | 66232.7 | 61763.5 | 2876.1 | 3965.5 | 9826.3 | |
| 165 | 69252 | 62782.7 | 3467.1 | 5084.9 | 10280.4 | |
| 180 | 62378.1 | 56176.1 | 4137 | 6517 | 10546.8 | |
| 195 | 57593 | 58044.3 | 5390.5 | 7267.4 | 10596 | |

| runs | x distance between plasma reactor center point and ozone probe | y distance between reactor center point & ozone probe | Total distance |
|---|---|---|---|
| 1 | 0 mm | 5 mm | |
| 2 | 0 mm | 5 mm | |
| 3 | 2 feet | 0 feet | |
| 4 | 2 feet | 0 feet | |
| 5 | 2 feet | 4 feet | |

Example DATA Sheet for Compact Portable Plasma Reactor

PHYSICAL CHARACTERISTICS

| Property | Typical value | Unit |
|---|---|---|
| Dimensions | 1.5 × 1.85 × 1.2 | inches |
| Net weight | <50 | g |
| Storage temperature | −40 to 80 | ° C. |
| Operating temperature | −40 to 80 | ° C. |
| Cycles of operation before the DBD electrode requires replacement | >1000* | |
| Cycles of operation with 2 (9 Volt) commercial batteries | >30* | |
| Ozone ($O_3$) emission levels | 120 to 349 | ppm |

ELECTRICAL PROPERTIES

| Property | Typical value | Units |
|---|---|---|
| Input voltage | 25 | V (DC) |
| Input current | 400 | mA (DC) |
| Max. input voltage | 60 | V |
| Max. input current | 1.5 | A |
| Output voltage | 6 | kVpp |
| Operating frequency † | 42 | kHz |

DBD PLASMA ELECTRODE CHARACTERISTICS

| Overall dimensions | 1.85 × 1.5 inches |
| Dielectric material | hydrocarbon/ceramics composite |
| Dielectric constant | 3.66 @ 8 to 40 GHz |
| Dissipation Factor | 0.0031 |
| Dielectric thickness | 0.030 inches (0.762 mm) |
| Electrode thickness | 1 oz. (35 μm) copper cladding |

Figure 15A:
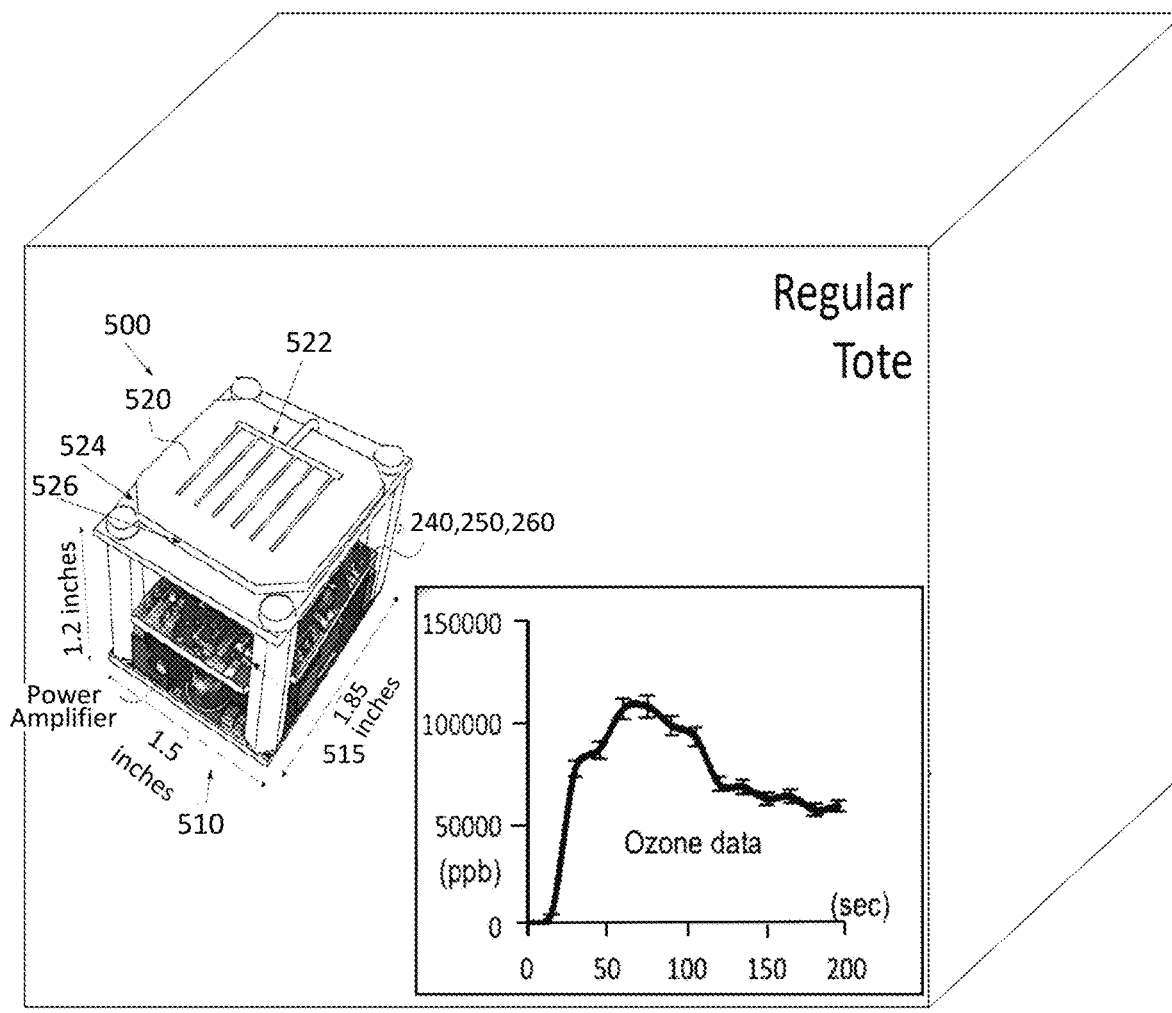
FIG. 15A shows the small, self-powered Active Packaging Module cube (inset) and corresponding ozone data (as in FIG. 2) within a commercial "Tote" shipping container (FIG. 15B).

*1 cycle equals to 3 minutes of continuous operation.
† Operating frequency may vary slightly according to the plasma electrode design An embodiment of the CPR is shown in FIG. 15A. This model runs on a single 9V battery. Testing for produce shelf life was done with CPRs added to standard containers with no additional change to the container or its contents.

Figure 15B:
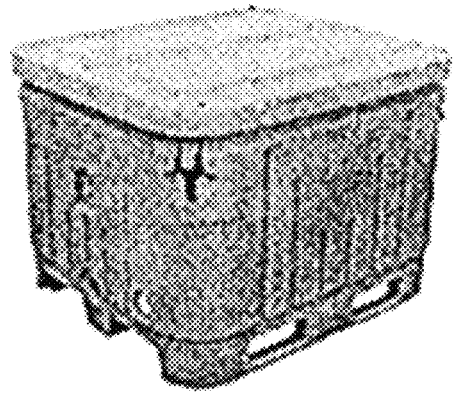
FIG. 15B shows a commercial "Tote" shipping container which can be incorporated into an embodiment of the subject invention.
Figure 16:
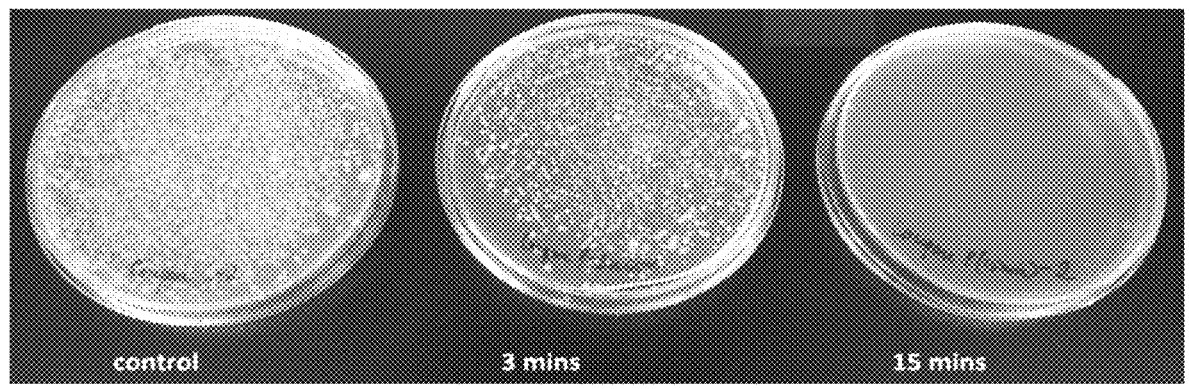
FIG. 16 Exposure of Green bean and tomato rot inoculum to ozone generated using 110V current. A $10^{-2}$ dilution plate for the control inoculum without plasma exposure and small duration (say x) and long duration (5x) exposer is shown on day 2.
Figure 17:
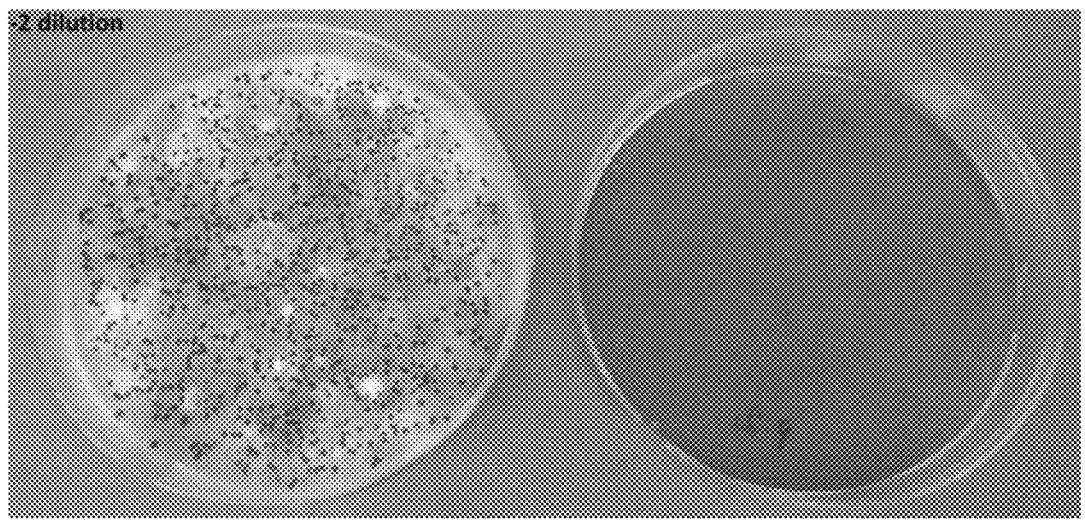
FIG. 17 Green bean and tomato spoilage organisms, control and with daily ozone treatment. Picture of 100 ul of 1:100 dilution of green bean and tomato inoculum spread on LB agar and incubated at room temperature for nine days. Plate on the left is the control. The plate on the right was exposed to ozone from a daily 3-minute plasma activation.

Coolers that were modified to permit monitoring of ozone levels were also used to test produce longevity at room temperatures. Room temperature storage containers can be designated as Green Box technology. Control and experimental (with CPR) containers were subject to the same environment conditions and tested following protocols established by the CPR and USDA. Another embodiment ran on two 9V batteries, and were activated and taped to the lid in storage totes (FIG. 15B). Similar sized coolers were used as test chambers, modified to allow ozone sampling. A single CPR was sufficient to produce enough ozone in a 2 cubic ft box to at least double the storage life of a variety of fresh produce types. Placing the CPRs in varying locations in the box did not affect the results.

The electrodes of the CPR can be designed in various geometries to increase the tridimensional flow of air and promote mixing of ozone and air inside the box.

An embodiment of the CPR device can operate in a household or commercial refrigerator, where the CPR runs on 110V AC current (a battery powered CPR can also be used in such refrigerators). CPRs to be used in refrigerators can connect with the electrical system of the appliance. Using standard ac current produces more predictable ozone production limits variation in ozone production, e.g., due to battery variation. The CPR was connected to a function generator for experiments, so that the power could be controlled and the effect of different levels of power could be determined. An embodiment of the CPR can operate at a single power level and use solid state components, rather than the bulky and more expensive voltage regulator.

To determine the amount of ozone produced by the CPR, the CPR was placed in a scaled chamber (324 cu. inch) that can be connected to an ozone monitor through were Teflon pipes running into the chamber. The experimental refrigerator was modified to allow it to be connected to the ozone analyzer as well. A literature search and preliminary data suggested that 1-10 ppm was sufficient to extend produce life (Glowacz and Rees 2016a; Glowacz and Rees 2016b; Gertzou 2016). In our system, a few minutes of the CPR activation was sufficient to produce at least 100 ppm in the produce drawer or small test chamber. For both ambient shipping and refrigerator use, a single CPR activation per day can be sufficient.

An embodiment can add ozone to atmospheric air surrounding produce at a target concentration of around 0.1 to 10 ppm, depending upon the inactivation and ozone sensitivity parameters for a given spoilage organism, in order for the ozone to kill most microorganisms. Ozone at this concentration also extends produce life and inhibits spoilage due to molds. Ozone also interacts with and decomposes ethylene that many types of fresh products emit, thereby retarding the produce becoming overripe by reducing their exposure to ethylene within the container. In addition, ozone is known to degrade pesticide residues (Swami S et al. 2016). Although ozone treatment kills bacteria and fungi, it is also known to extend produce shelf life. Ozone readily decomposes, leaving no residue.

We evaluated the ability of the CPR to extend the shelf life of produce at room temperature, refrigeration temperature, and to kill or inhibit growth of pathogenic and spoilage microbes. For these studies we used a variety of produce including green beans, strawberries, blueberries, roma tomato, green bell pepper, broccoli vine ripe tomatoes, cucumbers, lettuce and grape tomatoes. Experiments were done at least 3 times for reproducibility and were continued until the treated produce began to visually deteriorate. Different placement of produce within the container showed no effect as long as the produce was not sealed in airtight packaging.

An embodiment of the CPR can be used for GreenBox Testing at room temperature (tested at 21-25° C.). A concentration of at least circa 150 ppm ozone can be used, as increased heat and humidity reduces the efficiency of the technology as compared to refrigerator applications. The container can be treated with ozone each day, and experiments were conducted following this protocol, and produce was placed in a test container at room temperature. The produce was removed daily to take pictures of decomposition; the produce was then placed back in the bins and exposed to ozone. Shelf life varied with different batches of produce, but the shelf life was at least doubled by the ozone in each experiment and in some cases was extended four-fold.

In a similar manner, produce was held in a standard household refrigerator with one refrigerator drawer receiving a target amount of 100 ppm ozone from activating the CPR for less than a few minutes and a second identical drawer kept in an identical refrigerator without the CPR to generate ozone. A separate refrigerator was used as the drawers are not airtight and ozone generated in one drawer could affect produce in the adjacent drawer. In all cases, produce life was extended by refrigeration and the effect of ozone again at least doubled the storage life of the produce. A slightly lower amount of ozone was effective under the refrigerator conditions.

Inactivation of Spoilage Organisms and Human Pathogens by the CPR

We performed microbiologic research where we tested cocktails of bacterial foodborne pathogens and spoilage organisms and cultures of *Salmonella* strains recovered from outbreaks linked to tomatoes. Experiments that require the use of BSL2 pathogens were conducted in approved laboratories under the recommendations of the US Center for Disease Control (CDC) and the University of Florida Environmental Health and Safety division in the Emerging Pathogens Institute laboratories.

Our first trials were with the battery operated CPR. Pure cultures were grown overnight in L-broth and 100 µl of the culture was spread on a non-adsorbent glass or Teflon coupon. The coupon was placed in the test chamber with an CPR and exposed to ozone for different lengths of time. The coupon was then immersed in 5 mL of L-broth and vortex to remove surviving bacteria. Serial dilutions were plated, incubated for 48 hours and plated counts were compared to those of a coupon that was not exposed to the ozone. For experiments with the battery powered CPR, two test coupons were placed in a chamber with the activated CPR for 20 minutes the batteries were disconnected and the chamber left closed for an additional 20 minutes to allow the ozone to reach the maximum amount of impact. The coupons were then processed. This model killed >99% of a variety of Gram-negative bacterial pathogens. As seen in Table 1, counts of these bacterial were all reduced by about 2-logs (99%).

TABLE 1

Counts for the killing experiment with battery operated model

| Dilution | Log reduction with 20 minutes exposure | |
|---|---|---|
| | coupon 1 | coupon 1 |
| Serratia marcescens | 1.5 | 1.7 |
| Xanthamanas | 2.0 | 2.2 |
| Pseudomonas | 2.3 | 2.2 |
| Salmonella enterica | 2.1 | 2.4 |
| E. coli 0157 | 2.2 | 2.9 |

An embodiment of the CPR can be powered by the standard electrical grid. We expanded our produce selection to include more products that are typically stored under refrigeration. Daily ozonation of produce, using this set up and running the CPR for a few minutes each day, was shown to significantly increase shelf life of produce. Refrigerated storage has also shown similar efficacy. A single small duration exposure was sufficient to kill up to 99.9% of the highly concentrated, pure bacterial cultures (data not shown). For work with the ac grid powered CPR, we also moved to testing inocula made from inocula from produce purchased at local grocery stores and stored in a refrigerator at 5-8° C. until the produce was visibly spoiled. We worked with three different spoilage inocula. One was a combination of spoiled green beans and grape tomatoes; the second green leaf lettuce and cucumber, and the third was strawberries. The first inoculum was made from approximately 200 g of green beans and 100 g grape tomatoes. The second sample had 200 g each of butter lettuce and cucumber, and the third 200 gm of strawberries. We used a modification of the procedure of Mancinelli et al. The samples were placed in a sterile sample bag with 200 mL of LB broth with 20% glycerol and stomached for 5 minute. The supernatant of each sample was used as the inoculum and aliquots were frozen at −80° C. The standard small duration exposure had limited bactericidal effect. These produce preparations had a rich poly microbial population with both bacteria and fungi present. Three experiments were done with each slurry on coupons as describe above. We also tested a culture of *S. enterica*. A $10^{-2}$ dilution plate for the control and each exposure time from one of the green bean emulsion experiments can be seen in FIG. 11.

A complete microbial work up was not feasible, but the most abundant organisms in the green been sample were *Enterobacter* sp., *Chrysobacter* sp., and an *Aspergillus* sp. The lettuce and cucumber had *Xanthomonas* and *Chromobacter* and the Strawberries has *Fusarium* sp and *Enterobacter* sp. Increasing exposure time to 15 minutes resulted in >99.9% killing drop (Table 2).

TABLE 2

Counts for the Killing Experiments

| Inoculum source | Log reduction with 15 minutes exposure |
|---|---|
| Green bean and tomato | 3.6, 6 |
| Lettuce and cucumber | 5.2, 4.8 |
| Strawberry | 6.7 |
| *Salmonella enterica* | 4.2 |

We also wanted to determine if the plasma/ozone exposure contributed to extended storage by inhibiting the growth of spoilage organisms as well as the lethal effects. For these experiments, we used the inocula described above. Exposing inoculated plates, rather than microbes on coupons, to the ozone allows us to see the combined effect of inhibition of growth as well as outright killing of the organisms. The ozone may also be more effective when the organisms are present at a lower concentration that in the overnight cultures.

Duplicate sets of serial 1:0 dilutions of the inoculum were spread on LB plates and one set of plates (without lids) was exposed to ozone by running the CPR in our 324 cubic inch chamber with an input voltage of 25 V and a current of 430-440 mA. For the test plates, the CPR was run for three minutes every day and the chamber was left closed for approximately 24 hours between ozone exposures. The plates were taken out to be photographed and counted each day before the next ozone exposure. Both sets of plates were incubated at room temperature. The control plates were not exposed to ozone. The final plate count was the number after the mold colonies were recognizable at about 4 days. At this point, colonies were stable and not enough time had passed to allow secondary mold colonies to arise from spores. The pH of the L-agar plates remained the same after ozone exposure and the organisms grew normally on plates pre-exposed to ozone, so the inhibitory effects are not due to changes in the agar. All inocula resulted in heavy growth of flora with a mixture of microbes with spore forming mold and Gram-negative bacteria being the most common elements (FIG. 10). The plate counts reached their maximum after 3-4 days growth, with the fungi tacking longer to appear. Only a few minutes per day plasma activation was sufficient to produce a distinct inhibition of growth and/or killing of the organisms. Each experiment was done in triplicate.

TABLE 3

Log reduction after plasma exposure

| Inoculum | CFU log reduction on 3 minute APM exposed plates |
|---|---|
| Green bean and tomato | 5.13, 7, 6 |
| Lettuce and cucumber | 6.7, 2.6, 7.7 |
| Strawberry | 6.2 |

The CFU of organisms exposed to plasma was always reduced, usually by more than 5 log, after ozone exposure. We also saw a tendency for mold colonies on the ozone exposed plates to sporulate 24-48 hours later than on the control plates. There was considerable variation in the overall reduction of colony formation.

We have experimented on microbes isolated from rotten green beans, tomatoes, lettuce and cucumbers, and strawberries to observe how much killing/inhibition can be achieved by exposing plates plated with a solution of these vegetables to ozone created by the plasma actuators. Three experiments were performed on each inoculum (except strawberries) and these experiments demonstrated that plasma exposure can successfully inhibit the growth of both bacteria and mold species found in spoiled produce. Moreover, several of these experiments resulted in a greater than 5 log reduction of microbial colonies. It is not yet clear how much of the reduction in spoilage microbes is due to killing and how much is due to inhibition of growth. Colony sizes are identical on plates regardless of exposure. More work will be needed to determine the percentage of isolates killed versus inhibition of growth, but inhibition and killing of microbes appears to be an important component of the plasma/ozone's ability to prolong produce shelf-life.

TABLE 4

Example of Specification Sheet for One Embodiment of CPR

PHYSICAL CHARACTERISTICS

| Property | Typical value | Unit |
|---|---|---|
| Dimensions | 1.5 × 1.85 × 1.2 | inches |
| Net weight | <50 | g |
| Storage temperature | −40 to 80 | ° C. |
| Operating temperature | −40 to 80 | ° C. |
| Cycles of operation before the DBD electrode requires replacement | >1000* | |
| Cycles of operation with 2 (9 Volt) commercial batteries | >30* | |
| Ozone ($O_3$) emission levels | 120 to 349 | ppm |

ELECTRICAL PROPERTIES

TABLE 4-continued

Example of Specification Sheet for One Embodiment of CPR

| Property | Typical value | Units |
| --- | --- | --- |
| Input voltage | 25 | V (DC) |
| Input current | 400 | mA (DC) |
| Max. input voltage | 60 | V |
| Max. input current | 1.5 | A |
| Output voltage | 6 | kVpp |
| Operating frequency † | 42 | kHz |
| DBD PLASMA ELECTRODE CHARACTERISTICS | | |
| Overall dimensions | 1.85 × 1.5 inches | |
| Dielectric material | hydrocarbon/ceramics composite | |
| Dielectric constant | 3.66 @ 8 to 40 GHz | |
| Dissipation Factor | 0.0031 | |
| Dielectric thickness | 0.030 inches (0.762 mm) | |
| Electrode thickness | 1 oz. (35 µm) copper cladding | |

*1 cycle equals to approximately 3 minutes of continuous operation.
† Operating frequency may vary slightly according to the plasma electrode design CPR Lifetime: To estimate the life expectancy of an embodiment of the CPR, a module was activated for a few minutes and then turned off for nearly twice that time to simulate a small duration daily activation cycle. This cycle was repeated several times. The chamber was flushed with room air between cycles. After every 30 runs the ozone was measured. The run parameters were 25V, 385 mA. As shown in Table 5 (below), the device ran for at least 120 cycles. The ozone concentration after an activation run varied between 120 and 349 (this corresponds to approximately 4 months and 1 year of operation, respectively), consistent with what we saw for runs of multiple new CPRs, but with no clear evidence of loss of function.

TABLE 5

Ozone Production After Initial and Every 30 Cycles

| # of Runs | Ozone ppm |
| --- | --- |
| 1 | 315 |
| 30 | 236 |
| 60 | 120 |
| 90 | 349 |
| 120 | 215 |

The data suggests the reactor can be used for at least 4-6 months assuming it is turned on once a day. The weakest part of this reactor is its electrodes which may erode over time.

Traditional Ozone generators that could be used for food containers are bulky, consume high levels of battery power or require AC power to operate. An embodiment of the invention can incorporate a very low cost CPR printed circuit board assembly with integrated battery and data logger chip. The CPR can be recycled, or disposed of after shipment. The CPR can be placed on top of the shipment contents, or other location within the tote, just before the tote is closed. The CPR can switch on and off as needed and operate over the entire distribution chain. An inexpensive RFID data logger can be added on the CPR printed circuit board design. The RFID chip can store basic environmental and quality control parameters and can be read by a standard handheld RFID reader. The CPR can be read in place, before or after the tote is opened, or removed and read when the customer opens the tote. The CPR can be removed, reset, recycled and/or disposed as needed.

Example—Greenbox

One embodiment of the present invention is to decontaminate air and surfaces employing an integrated plasma generating circuitry inside of a partially sealed, or completely sealed, container via diffuse electrical plasma generated in atmospheric air, such as an environment originally of atmospheric air and which is ozonated with some time cycle. This is accomplished by applying a potential difference between two electrodes, separated by an insulating dielectric layer. An embodiment of the GreenBox system consists of a container with integrated circuitry, an external power supply, a disposable plasma actuator, and a timer.

Description of Operation

Vegetables and other perishables, including but not limited to nuts, seeds, grains, fruits, pastries including dairy based pastries can be added to an embodiment of the GreenBox system, to help extend their shelf life as compared to open air or refrigeration alone. The box is intended for home use, transportation, or retail. It can be used in a refrigerated environment and the full operational range is defined in the Data Sheet.

Perishables are added to (e.g., placed in) the box, the box is then closed, and the ozone producing system can be turned on, or operated, according to a desired time cycle. In an embodiment the user can turn the system on with the switch on the power supply. Optimal time to fill the container with ozone is 5-15, 6-14, 7-13, 8-12, 9-11, and/or approximately 10 minutes. After this time, the user can turn the system off. Before opening the container, to ensure most of the ozone has decomposed to oxygen and that the ozone has had a change to have an effect on microbes and ethaline, the user should wait for a "working period" of 40-80, 5-70, 55-65, and/or about 60 minutes. After this time period, e.g., 60 minute period, the ozone levels drop to below the NIOSH recommended exposure limit of 0.1 PPM. The period is longer if the unit is used in temperatures below a temperature of 20 Celsius.

One of the benefits of the green box design is that it does not require continuous operation of the plasma electrode. Our numerous tests have demonstrated that running the plasma circuit for only a few minutes a day is enough to halt the reproduction of bacteria and insect pests and prolong the life of produce and grain. Therefore, a time controlling module is added to the green box to operate the plasma electrode in a particular interval of time during day/night. This mechanism increases the lifespan of the GreenBox system, reduces energy consumption and regulates ozone to safety levels when the box is open. The timer component of the system will have a clock with which the user can set the time of day they wish the unit to activate. The system can activate at the same time every day, say middle of the night when access to the perishables is not necessary. A light will indicate when the system is running, when it is in its "working period", and when it is appropriate to open. FIG. 2 shows a maximum ozone concentration in a 3 cubic foot box, the time to reach that concentration, and the time for the ozone to decay to lower concentrations. A system diagram is shown in FIG. 1.

To further ensure safe handling, other iterations include a switch that does not allow the user to turn the system on unless the lid is closed.

In a specific embodiment, the GreenBox system consists of the container with integrated circuitry, an integrated control timer, external power supply, an actuator module, and disposable plasma actuators. A module in which the actuator is inserted to be powered is the only thing exposed in the box. A shield on the actuator can let air out but keep the circuit from short circuiting via wet surface contact.

The box interior can be constructed of ozone resistant plastic or lined with an ozone resistive coating. The box insulates the perishables when the box is being transported or used outside of room temperature conditions. Similar to a cooler, the box consists of two layers of plastic filled with insulating foam. A hinged top can be opened, closed and latched shut. The top is air-tight to keep ozone from escaping during operation. An air tight seal is achieved with an ozone resistive gasket lining the top and box that forms a seal when the top is brought down and latched closed. The top will pivot on two hinges and can be kept shut with two latches. Integrated inside one of the small upright walls of the cooler will be the plasma generating circuitry (position shown in FIG. 4 and FIG. 5). The circuitry is inaccessible and thermally and electrically insulated inside of the wall. Materials such as Silicone and thermally insulating sheets are used to this end. There is a small DC jack input on the outside of the box on the same wall as the circuitry (FIG. 2). This is where the power supply is plugged in and subsequently unplugged for easy transportation. The box remains plugged in while the cycle is running but may be moved when in cool down mode. Wires lead from this port to the circuit through the interior of the wall. The output of the circuitry is fed out of the wall (interior of the box) and attached to the actuator module which itself is affixed to the wall (FIG. 4). Other sets of wires lead from the circuitry to the programmable timer which is located on the wall adjacent to the circuit and actuator module (FIG. 3). An LED indicator is located above the timer and will signal to the user if the system is ready to use, when the system is in use and when it is not advisable to open.

In one embodiment, the box contains a fan unit which in operation circulates ozone within the box. Another embodiment contains a fan and catalytic ozone scrubber located on a wall of the box. This ozone scrubber pulls air out of the interior volume of the box and passes it through a metallic catalyst capable of reducing the ozone into oxygen before it reaches the exterior of the box. The ozone scrubber module is located near the bottom of the wall where the ozone concentration is highest from settling. The ozone scrubber will use replicable catalyst cartridges.

A specific embodiment relates to the CPR shown in FIGS. 10, 11, and 12, and incorporates the circuitry shown in FIGS. 23 and 24, operated as follows:

Parameters:

Output AC voltage: An embodiment of the CPR supplies a voltage of approximately 6 kVpp to produce plasma. Depending on the dielectric material of the plasma reactor or if the CPR is an arrangement, it is possible to supply other values of the output AC voltages, which can range from 1 kVpp to 50 kVpp.

Output Current: An embodiment of the CPR embodiment supplies an output AC current in the order of μA. Depending on different modifications and if they are connected in arrays, the output AC current could range in the range 1 μA to 1 A.

Input DC Voltage: The current CPR consumes an input DC voltage of 25 V. However, the input voltage can vary in a range of 10 to 60 V.

Input DC Current: The CPR prototype requires a DC input current of 400 mA for activation. However, other versions of this could consume an input DC current in range of 100 mA to 10 A or more.

Operating Frequency: 1 kHz to 300 kHz.

Size: the size of CPR embodiment is a stack with dimensions A×B×C. (0.1 mm<A,B,C<100 mm). In addition, the circuit can be separated into different modules that can be arranged in a 2-dimensional fashion.

Embodiments of the present invention comprise a water treatment system based on an ozone producing Dielectric Barrier Discharge Plasma generator.

Figure 26:
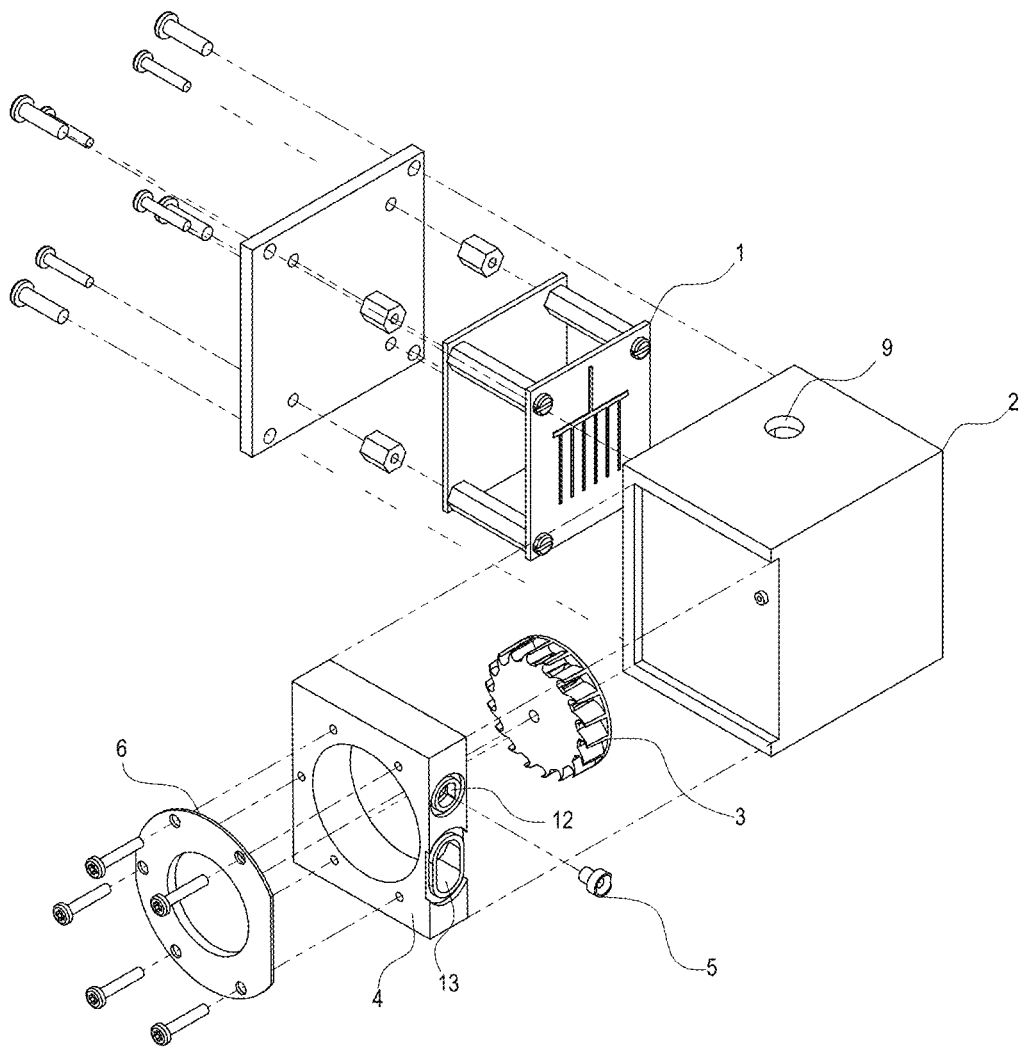
FIG. 26 shows the components of a water treatment system, including a mixing chamber, a powered electrode, and a mixing wheel.

Herein PurplePure refers to the ozone producing, and initial mixing portion of the system (FIG. 26). Active Plasma Module (APM) refers to the Ozone generating portion of the PurplePure, consisting of circuitry and a replaceable DBD electrode. The device functions with an external flow or water pressure to the inlet.

Figure 25:
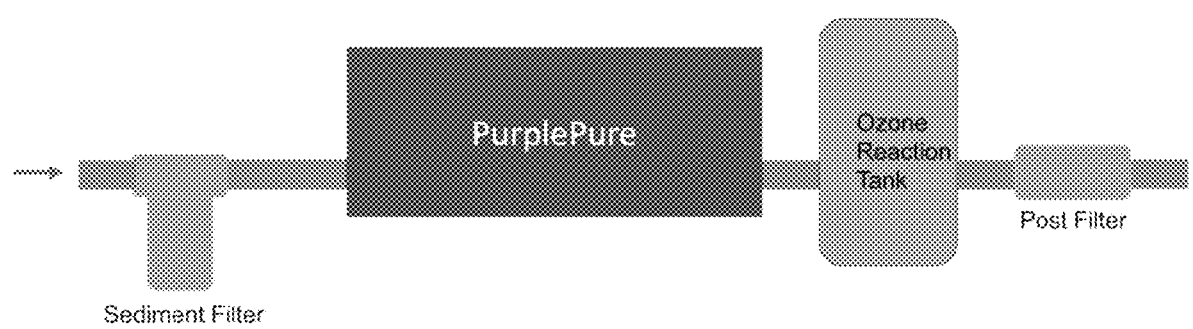
FIG. 25 shows an embodiment of a water treatment system incorporating a sedimentation filter and an external water pump.

Embodiments of the subject invention relate to an apparatus and method for treating water for drinking. In specific embodiments, the apparatus includes an ozone generator that generates ozone for mixture into the liquid, an AC to DC power supply, a venturi injector to mix the generated ozone and liquid, and a chamber into which ozonated water can be delivered where it reacts with and eliminates contaminates, and involves an end filtration step to remove remaining ozone and precipitated particulates. In further embodiments a sedimentation filter is included in the water stream before the treatment system and an external water pump is included to introduce untreated source water to the system. A schematic of an embodiment of the subject system is shown in FIG. 25.

Figure 27:
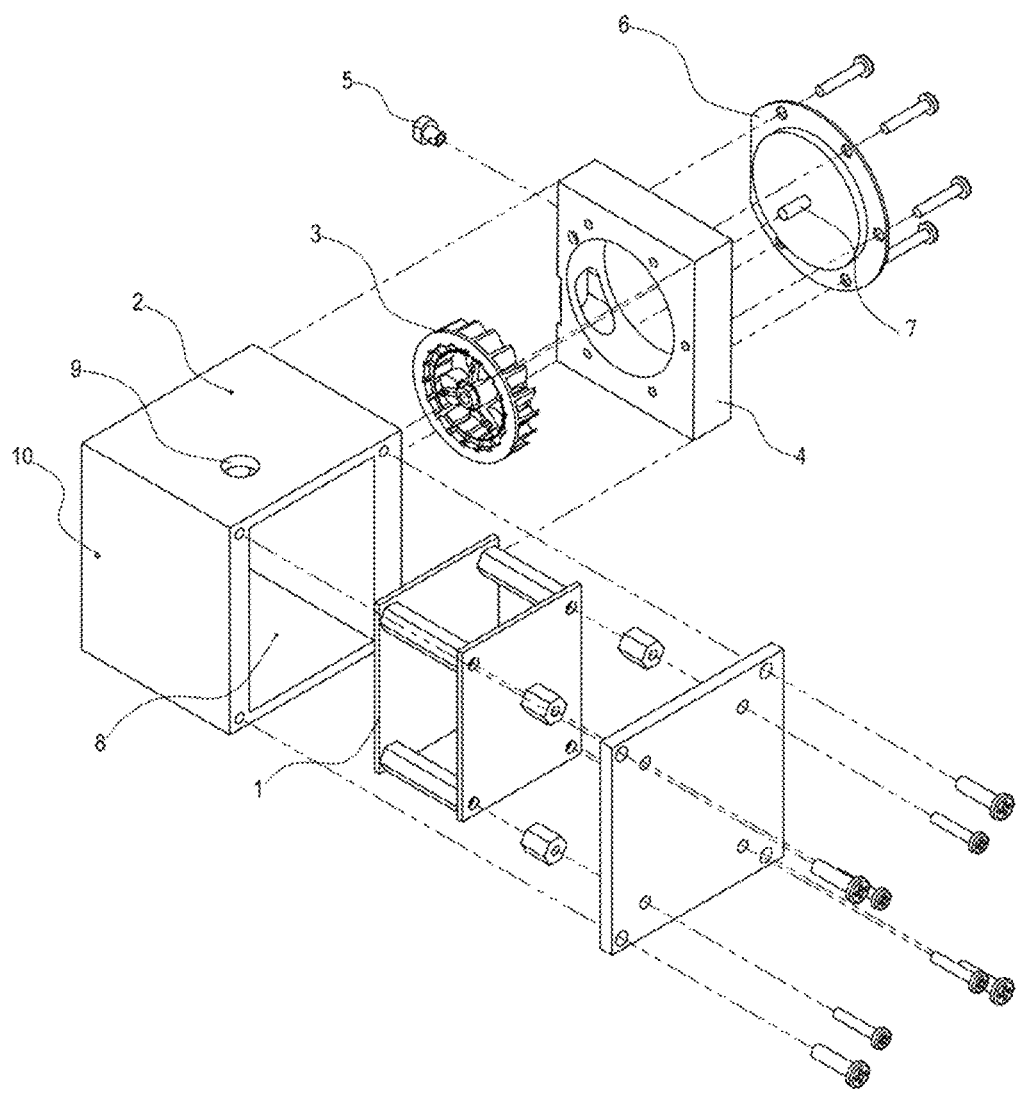
FIG. 27 shows the embodiment of FIG. 26 from a different perspective.

Some ozone water treatment systems draw a large amount of power, whereas specific embodiments of the PurplePure only requires 10 Watts or 25 volts and 400 milliAmps. Power is provided to the APM by an AC to DC power supply. The power supply can operate off of a wall power socket that can provide either 120 or 220 volts AC. The power supply interfaces with the APM through a male dc jack that can be plugged into the APM via a small hole 9 in the APM housing (FIG. 27).

Existing ozone water treatment systems produce and transfer too high of concentrations of ozone into the water to be treated resulting in concentrations of ozone that are higher than required for water treatment and above the FDA GRAS limit of 0.4 PPM in water. A major concern of excess ozone concentration in water is the formation of Bromate. Fortunately, if the ozone treatment process parameters are adjusted carefully (such as avoiding excessive ozonation), the bromate formation can be limited to levels below the MCL (10 ug/l).

Embodiments of the subject water disinfection system transfer Ozone concentrations below this limit. Embodiments of the subject system require the untreated water to have an external force to drive it through the system. This includes an external pump, or in some iterations, a direct integration to a household faucet end. In a specific embodiment the pressure of the household water supply will drive the water through the treatment system.

In FIG. 26, the main components include a piping inlet and outlet to the mixing chamber (4), venturi injector (4), APM including the powered electrode (1), and mixing wheel (3).

Figure 28:
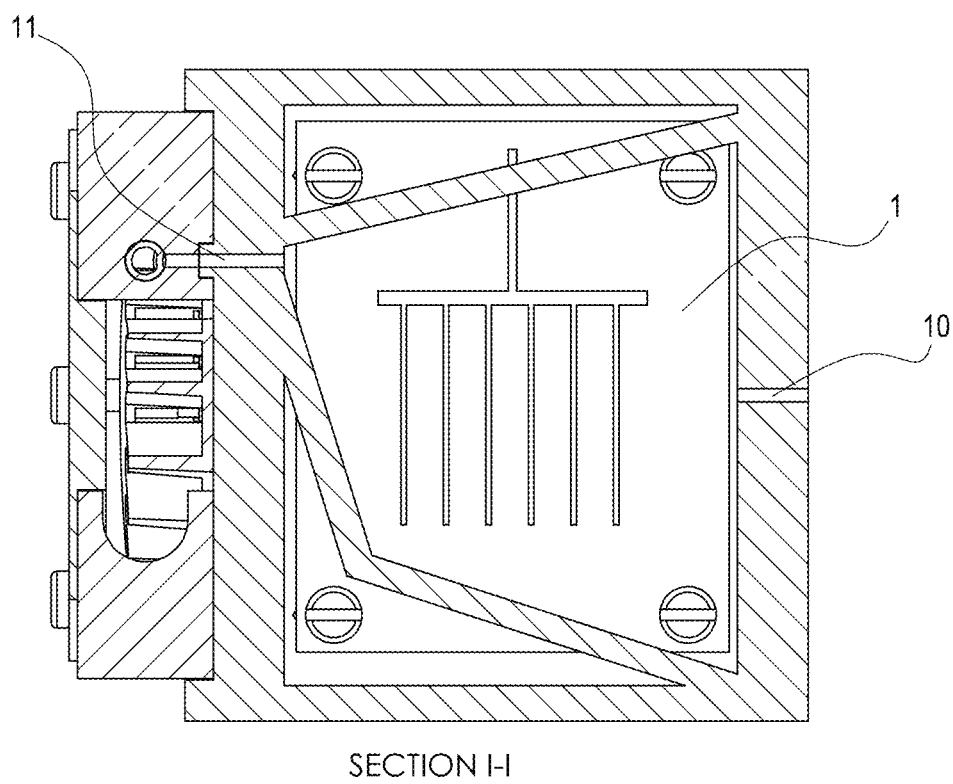
FIG. 28 shows an embodiment of an active plasma modulator.

Ozone is generated by the APM in chamber (2). The APM needs a supply of fresh air to break up the $O_2$ molecule to form Ozone. Fresh atmospheric air is fed in through a small hole (10) on the side of chamber (2). There is a non-direct path for the air to travel through the hole. This is accomplished by adding a maze-like structure for the air to flow through. A negative pressure (discussed later) causes the air to flow in to the chamber through the non-direct path and when the negative pressure is off, the interior of the chamber (2) should be at atmospheric pressure the same as outside of the chamber. This equal pressure means that ozone that is remaining in the chamber (2) would have to find its way out of the chamber, through the maze, by random collision (there is a low probability of ozone molecules doing this). Chamber (2) is connected to the interior volume of (4) by a small hole (11). As ozone is produced in chamber (2) it is sucked in to chamber 4 through the hole (11) connecting the two via a channel on the surface of the APM 1 shown in FIG. 28. Ozone is only produced on the surface of the APM (above the powered electrode (1)) this is further restricted to be in the volume enclosed by the channel (FIG. 28). The channel allows a high ratio of ozone to air to be sucked in to the chamber (4) because the flow of the air is constricted to be along the region where ozone is being produced. The electrode of the APM is replicable and once the dielectric material or powered electrode is degraded it can be extracted through a narrow slit in the side of the APM housing (2). A new electrode is inserted in its place.

As the water flows into (4) via (12) it passes through the venturi injector (5). The velocity of the water decreases then increases as it flows in and out of the injector. This change in velocity results in a negative pressure near the exit flow (of the venturi) into chamber (4). There is a small port in chamber (4) located on the side of the outlet of the venturi injector (normal to the flow of water) closest to the interior of the chamber (4) where the pressure is negative, and the ozone gas is sucked in from chamber (2). The ozone gas is mixed with the water by the introduction to the water flow and by the mixing wheel (3).

Figure 29A:
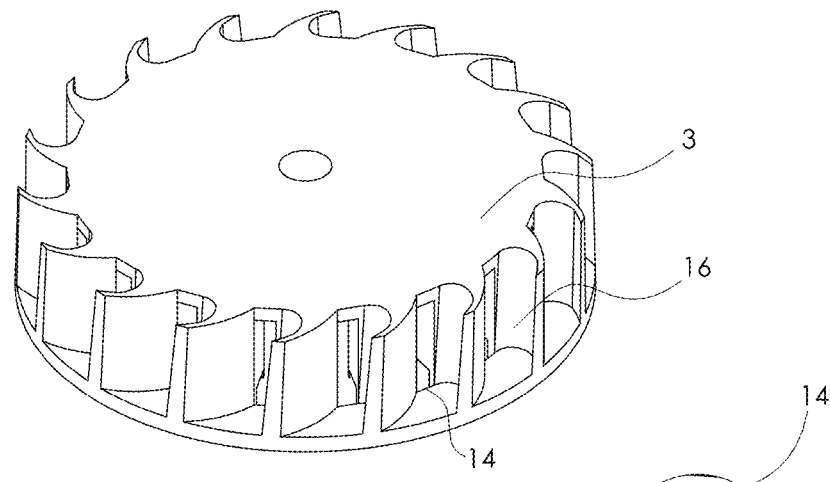
FIG. 29A shows a view of a mixing wheel.
Figure 29B:
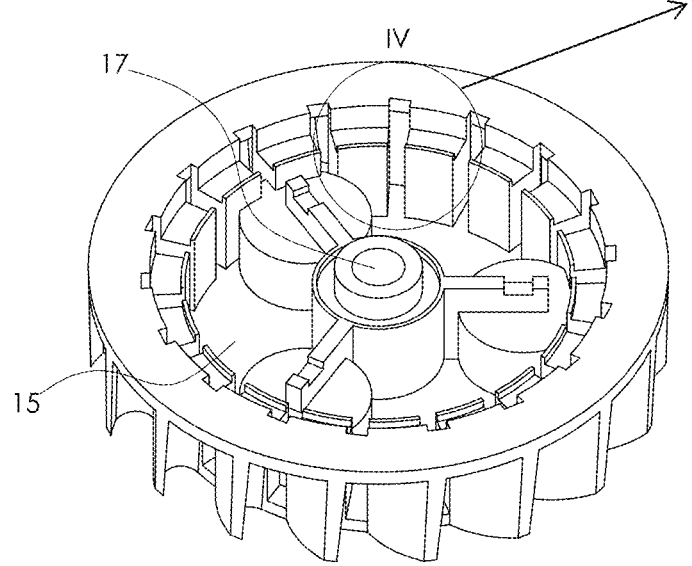
FIG. 29B shows the mixing wheel of FIG. 29A from a different perspective.

The mixing wheel is detailed in FIGS. 29A-29B. When water hits the wheel after exiting the venturi injector some of it passes through small slits (14) in the bucket grooves (16) of the wheel. It then travels to the cavity at the center of the wheel (15). The water builds pressure in this cavity and pushes the wheel away from the wall of (2). In this sense the wheel is self-lubricating, eliminating any friction of the wheel against the wall of (2). The wheel is centered and the buckets are kept from rubbing the circumference of the mixing chamber in (4) by an axel (7) which runs through the central hole of the wheel (17) and is attached to the piece (6) that seals the wheel in chamber (4). This aforementioned piece to which the axel is attached sits opposite on chamber (4) from chamber (2).

Water exits the mixing chamber through the exit port (13) and travels down piping to an ozone reaction tank. The water settles in the tank to fully kill off any bacteria present in the water. After the water sits for a reaction period it travels down the line to a filter which removes any remaining ozone in the water through absorption or catalytic decomposition. Any precipitated metals are also removed by this final filtration step.

Data

TABLE 6 values and ranges for the ozone generating circuit.
Electrical Properties

| Property | Typical value | Units |
| --- | --- | --- |
| Input voltage | 25 | V (DC) |
| Input current | 400 | mA (DC) |
| Output voltage | 2-14 | kVpp |
| Output frequency | 5-50 | kHz |

Embodiments of the Purple pure system meet the optimal concentration of 0.1-0.3 PPM of ozone in the water flow. For both near instantaneous and long-term flow conditions the concentration of ozone transferred to the water sits between 0.1-0.3 PPM. Data collected from 10 samples of ozonated water using an embodiment of PurplePure is shown in Table 7.

TABLE 7

Ozone mixed in water using one arrangement of PurplePure.

After 4 seconds

| Sample # | Ozone Concenteration in water (PPM) | Statistical Analysis | |
| --- | --- | --- | --- |
| 1 | 0.09 | Mean | 0.183 |
| 2 | 0.12 | Standard Error | 0.01542365 |
| 3 | 0.2 | Median | 0.205 |
| 4 | 0.21 | Mode | 0.21 |
| 5 | 0.21 | Standard Deviation | 0.04877385 |
| 6 | 0.21 | Sample Variance | 0.00237889 |
| 7 | 0.18 | Kurtosis | 0.06136472 |
| 8 | 0.21 | Skewness | −0.8450577 |
| 9 | 0.25 | Range | 0.16 |
| 10 | 0.15 | Minimum | 0.09 |
| | | Maximum | 0.25 |
| | | Sum | 1.83 |
| | | Count | 10 |

Figure 30:
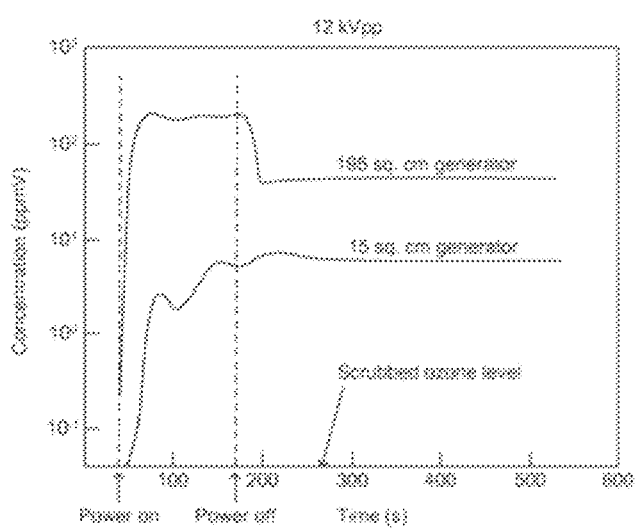
FIG. 30 shows a graph of ozone generation as a function of plasma reactor surface area.

Based on previous research, the active plasma cube reactor will employ a set of electrodes separated by an insulator and differentially powered at a radio frequency (RF) with an external electric circuit. This patented and patent pending design (R. Chinga, K. Zawoy, S. Roy and J. Lin, U.S. Pat. No. 9,774,239 dated Sep. 26, 2017; S. Roy and S. Portugal, "Compact Portable Plasma Reactor" filed on Dec. 29, 2017 as Ser. No. 62/612,027) provides the framework to develop further patented innovations (K. Zawoy, S. Roy and D. Pituch, Method and Apparatus for Disinfecting and/or Self-Sterilizing a Stethoscope using Plasma Energy, U.S. Pat. No. 9,056,148 B2 dated Jun. 16, 2015; S. Roy, K. Zawoy, Self-sterilizing device using plasma fields, U.S. Pat. No. 9,757,847 dated Sep. 12, 2017) and to produce sufficient plasma flux and high ozone generation capacity. We have collected data on ozone generation as a function of surface plasma generator size (FIG. 30).

Figure 31:
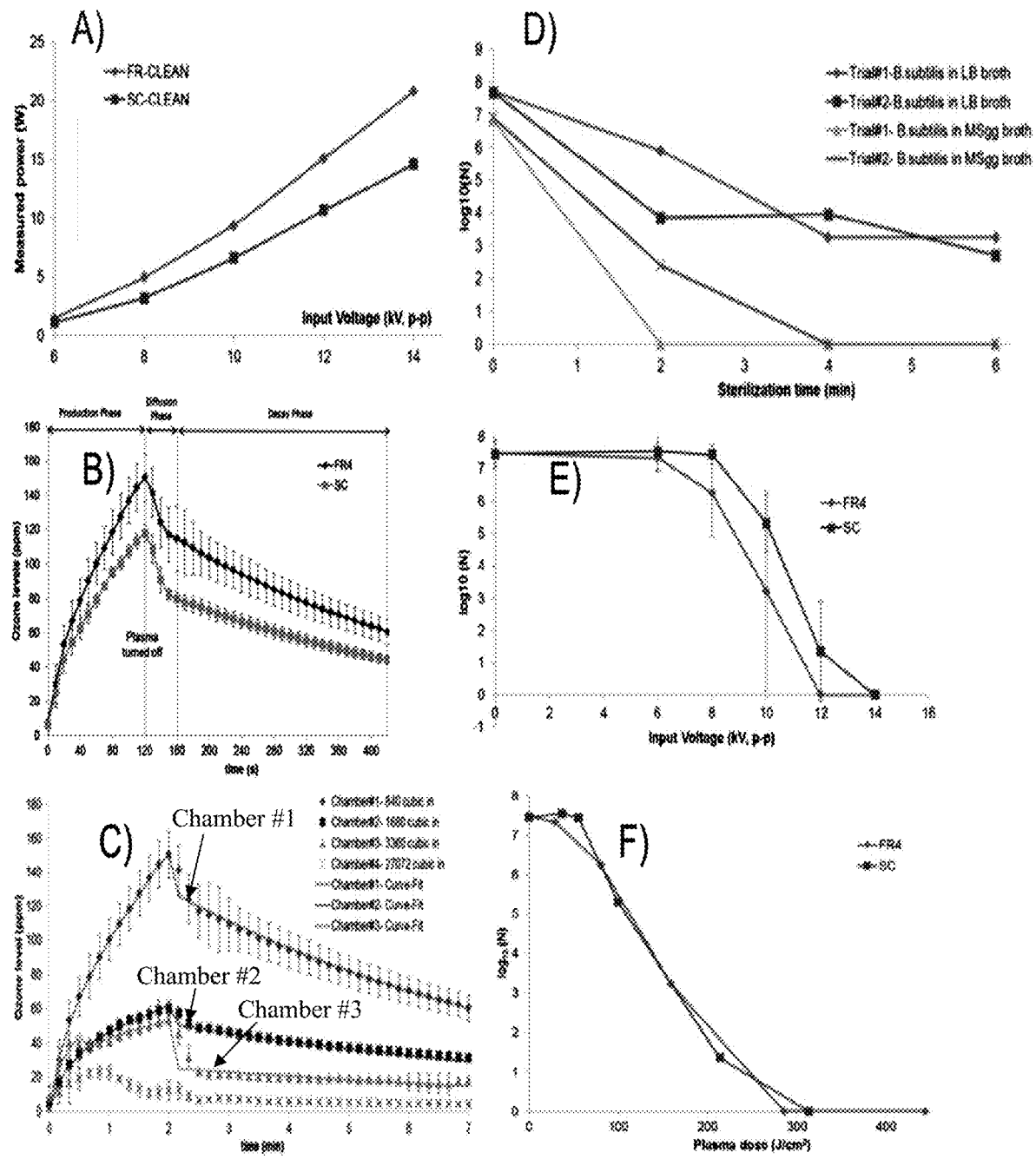
FIGS. 31A-31F show the effect of surface plasma and ozone gas on decontamination and sterilization.
Figure 32:
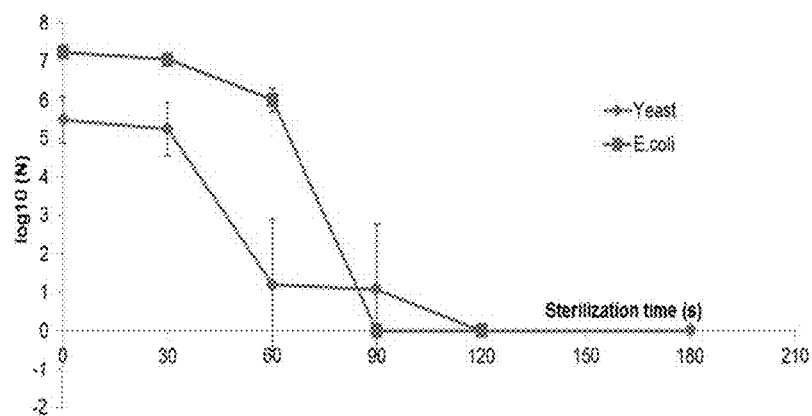
FIG. 32 shows survival curves obtained using DBD decontamination of Yeast strain *S. cerevisiae* and *E. coli*.

Aggregate experimental data from a previous study (N. Mastanaiah, P. Banerjee, J. Johnson and S. Roy, 2013, "Examining the role of ozone in surface plasma sterilization using dielectric barrier discharge (DBD) plasma," Plasma Processes and Polymers, 10, 1120-1133 (appeared as the cover article for December 2013 issue)) is presented in FIGS. 31A-31F below. Among the illustrated principles applicable to the Ozone Module component of embodiments of the subject water treatment system are the relationships between input voltage and measured power output and plasma generation (FIG. 31A), the time course, phases and concentration of ozone generation and persistence using different dielectric materials (FIG. 31B), and within various scaled volumes of enclosures (FIG. 31C), for measurements of log reductions in microbiological counts over time including a resistant spore former (FIG. 31D), and with respect to voltage (FIG. 31E), and plasma dosage (FIG. 31F).

Research on a Water Ozonation System for Bacterial Decontamination

Experiments have been conducted using surface plasma for sterilization purposes and demonstrated the efficacy of surface plasma in producing log reductions of 6 or higher using a wide variety of BSL-I and BSL-II pathogens. After 4-6 minutes of plasma exposure, organisms were variously susceptible to plasma, exhibiting complete ~6 log reduction in 4 minutes. FIGS. 32A-32F shows survival curves obtained using our plasma tiles with BSL-I organisms such as *Eschericia coli* and Yeast. BSL-II pathogens including *Staphlococcus aureus, Salmonella enterica* and Vancomycin resistant enterococci (VRE) were also tested as summarized in Table 8, with most pathogens showing 7-8 log reduction after 3-4 minutes of plasma exposure.

The fundamental mechanism of surface-plasma based sterilization has also been studied, concluding that, of the numerous factors involved during plasma generation (UV, reactive oxygen species and heat), reactive oxygen species such as ozone played a pivotal role in destroying microorganisms.

TABLE 8

Results from Plasma Sterilization Experiments with BSL-II pathogens

| Type of Pathogen | Sterilization time (min) | Observed Reduction | Complete Inactivation | Cell Type |
|---|---|---|---|---|
| *P. aeruginosa* 6003-7 | 2 | 8 log | Yes | G− |
| *Y. enterocolitica* SSUD 4037 | 2 | 8 log | Yes | G− |
| *S. enterica* EPI 6031 | 3 | 7 log | Yes | G− |
| *Listeria monocytogenes* | 3 | 8 log | Yes | G+ |
| Vancomycin Resistant Enterococci (VRE) | 3 | 8 log | Yes | G+ |
| *Escherichia coli* | 3 | 8 log | Yes | G− |
| *Vibrio cholera* | 3 | 8 log | Yes | G− |
| *Acinetobacter baumannii* | 3 | 4 log | No | G− |
| MRSA WCH132 | 2 | 3 log | No | G+ |

Figure 33A:
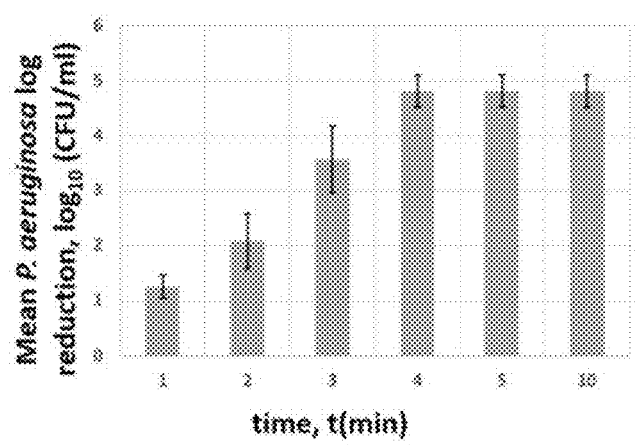
FIG. 33A shows the mean log reduction of *P. aeruginosa* in water versus time over all the repeated active ozonation experiments.
Figure 33B:
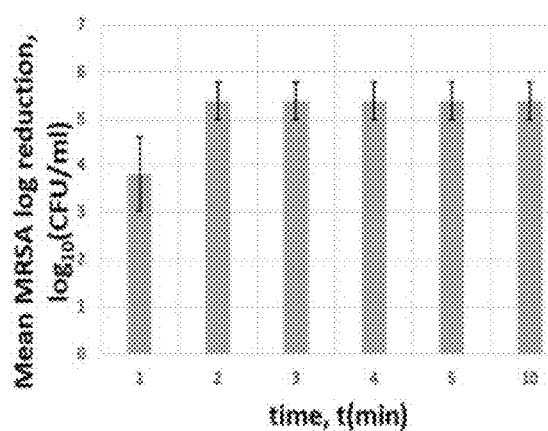
FIG. 33B shows the mean log reduction of Methicillin-resistant *Staphylococcus* (MRSA) in water versus time over all the repeated active ozonation experiments.

Ozone is a well-known disinfection agent for contaminated water which is used as an alternative for chlorine in many applications. We have investigated deactivation influence of exposure time of ozonated water and input energy for two bacterial species: *P. aeruginosa* and MRSA. A surface dielectric barrier discharge plasma reactor was used in atmospheric conditions as the source of ozone production along with an air pump and a microdiffusion stone for mixing the ozone in water contaminated with *P. aeruginosa* and MRSA (see FIGS. 33A-33B). Bacterial inactivation was measured at six different time points from 1 to 15 minutes to find the threshold exposure time needed for complete deactivation of the bacteria. The corresponding ozone concentration in water as well as the input energy required to generate it was obtained as well. A log reduction of 4.8±0.3 in CFUs of *P. aeruginosa* in contaminated water was achieved in 4 minutes which corresponded to an ozone concentration of 0.09±0.06 mg/L and an input energy of 8.8±1.48 J. In case of MRSA, a log reduction of 5.4±0.4 in CFUs was achieved in 2 minutes, which corresponded to an ozone concentration of 0.07±0.06 mg/L along with an input energy of 4.4±0.74 J. Also the average power requirement for these experiments is about 2 watts.

Removal of Metals

Experimental method to test mercury (Hg) and lead (Pb) removal of the system is outlined below.

First, in order to establish the efficiency of embodiments of the subject remediation technology, synthetic water is used and spiked with known amounts of inorganic (inorganic carbon, phosphate, etc.) and organic (DOC) ligands to create gradients in concentrations, and then spiked with the selected metals, tested individually and in combination. The goal is the determination of parameters that lead to the removal of Hg and Pb down to <ppb levels and as low as 10-15 ppt.

Second, the determined optimum operation conditions for metal removal are then used and applied to actual water effluents containing Hg and Pb pollution.

Figure 34:
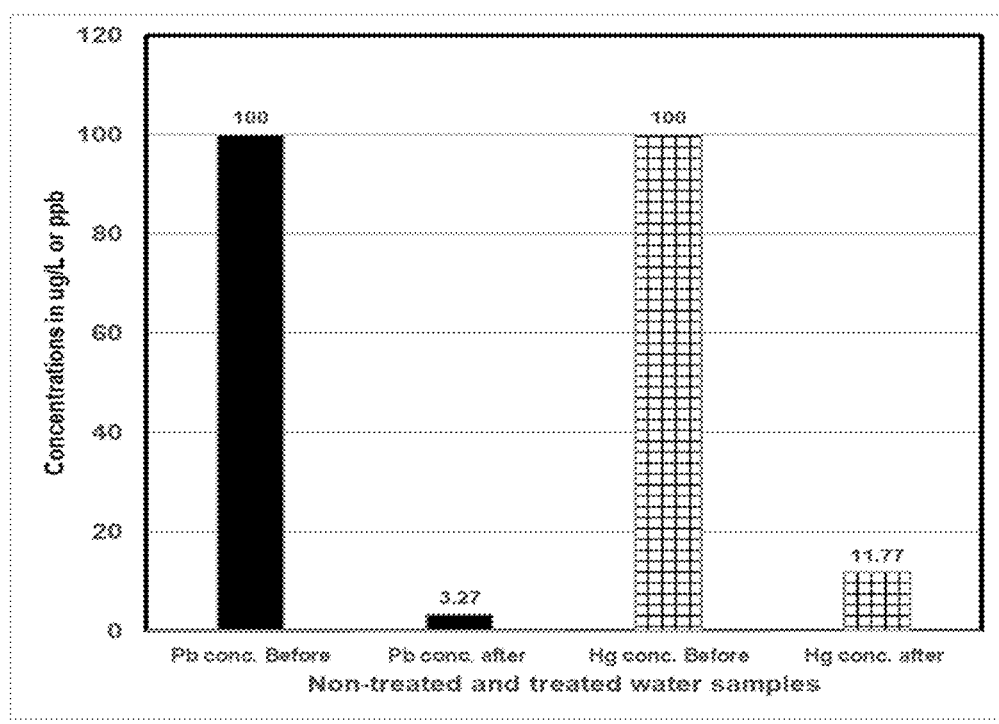
FIG. 34 shows the concentrations of lead (black bars) and of mercury (hatched bars) in water samples spiked at a final concentration of 100 mg/L (ppb) determined by ICP-MS before and after treatment with the proposed remediation technique.

Our preliminary results plotted in FIG. 34, using metal spiked distilled water at circumneutral pH, showed a significant decrease in both Hg and Pb concentrations as determined by inductively coupled plasma mass spectrometry (ICP-MS).

PFOA/PFOS Removal

An example of degradation of PFOA and PFOS by the water treatment system is shown here. We used water samples spiked with known amounts of standard PFOA and/or PFOS solutions obtained from commercial sources. This process helped increase PFCs concentrations far above the detection limits of the analytical method used in this study. Table 9 summarizes the different types of water treatments in the study.

TABLE 9

Sample preparation matrix for each water sample, PFCs spiked and non-spiked water samples were used comparatively.
Types of samples to be prepared for each wastewater type or drinking water

| Non-spiked (background) | Spiked with PFOA | Spiked with PFOS | Spiked with both PFOA & PFOS |
|---|---|---|---|

Methodology

PFOS and PFOA are relatively non-polar and were separated from other compounds in the water samples via reverse phase HPLC with a C8 column and utilizing a water and methanol gradient. With negative ion electrospray ionization, (−)ESI-MS, PFOS and PFOA readily produced their respective [M-H]— ions (M being the neutral molecule). With the samples analyzed to date, the (−)ESI-MS was sufficient for their detection.

With the quadruopole ion trap mass spectrometer used for these studies, collision-induced dissociation (CID) tandem mass spectrometry (MS/MS) is possible. The (−)ESI-MS of the m/z 413 [M-H]— ion of PFOA produced m/z 369 as the most abundant product ion with some additional relatively minor m/z 347, 219 and 169 product ions.

The (−)ESI-MS of the m/z 499 [M-H]— ion of PFOS only produce a series of low intensity product ions, m/z 169, 230, 280, 330, 380 and 419. Other MS/MS instruments show the major (−)ESI-MS/MS of m/z 499 product ions of PFOS as being m/z 80 and 99. Due to the low m/z cutoff of the quadruople ion trap mass spectrometer, it is not possible to detect the major m/z 80 and m/z 99 product ions of the m/z 499 [M-H]— ion of PFOS with internal MS/MS. Instead source collision-induced dissociation (SCID) was used. Optimum m/z 413 to m/z 369 occurred at SCID 10 V while m/z 499 to m/z 80 and 99 optimized at SCID 50 V. If the matrices become complicated, the MSn capabilities can be used for the determination PFOS and PFOA. Identification of degradation products. No attempt has been made to determine these at this point. However, the HPLC/ESI-MSn capabilities of the quadrupole ion trap make it a good choice to detect and provide structural information on degradation products. In addition to the quadrupole ion trap mass spectrometer, high resolution/high m/z accuracy HPLC/MS instruments are also available to provide data to aid in identification.

TABLE 10

Comparison of the peak areas of PFOA and PFOS for treated and untreated samples.

| Sample | Percentage left after Treatment | HPLC/(−)ESI-MS Peak Areas | |
|---|---|---|---|
| | | Treated | Untreated |
| PFOA | | | |
| DW | 3.06 | 93,827,715 | 3,067,708,445 |
| WWTP-1 | 0.00 | 0 | 1,020,433,864 |
| WWTP-2 | 0.00 | 0 | 1,790,245,766 |
| PFOS | | | |
| DW | 2.09 | 478,632,681 | 22,932,257,309 |
| WWTP-1 | 4.75 | 636,272,537 | 13,389,935,379 |
| WWTP-2 | 7.44 | 1,043,058,472 | 14,017,384,675 |

DW is deionized water and WWTP-1 and WWTP-2 are water samples from waste water treatment plants. All samples spiked with PFOA or PFOS.

EMBODIMENTS

Embodiment 1. A power supply system, comprising:
 a power amplifier connected to a load,
 wherein the at least one power amplifier comprises:
 a transformer; and
 an inductor,
 wherein the transformer is configured to:
 receive a supply voltage at an operating frequency; and
 output a supply power to the load at the operating frequency;
 wherein the power amplifier further comprises a variable capacitor in parallel with a transistor,
 wherein a resonance frequency of the transformer connected to the load is set based on values of the inductor and the variable capacitor, and
 wherein the variable capacitor is configured to be adjusted to tune its capacitance value to match an impedance of the power amplifier with an impedance of the load.
Embodiment 2. The power supply system of embodiment 1,
 wherein the variable capacitor is further configured to set a resonance frequency of the transformer connected to the load to match the operating frequency of the supply power.
Embodiment 3. The power supply system of embodiment 1, further comprising:
 a variable function generator configured to provide the supply power to the power amplifier.
Embodiment 4. The power supply system of embodiment 1, further comprising:
 a controller configured to control an input voltage to the power amplifier.
Embodiment 5. The power supply system of embodiment 4,
 wherein the input voltage is supplied in a duty cycle.
Embodiment 6. The power supply system of embodiment 4, further comprising:
 feedback circuitry configured to monitor an operational parameter of the load and provide feedback to the controller,
 wherein the controller is configured to control operation of the power amplifier based on the provided feedback.
Embodiment 7. The power supply system of embodiment 6,
 wherein the feedback circuitry comprises:
 a moisture sensor configured to detect moisture on an active surface of a plasma actuator,
 wherein the load comprises the plasma actuator.
Embodiment 8. The power supply system of embodiment 6,
 wherein the feedback circuitry comprises an air speed sensor configured to determine a speed of airflow over an active surface of a plasma actuator,
 wherein the load comprises the plasma actuator.
Embodiment 9. The power supply system of embodiment 1,
 wherein the variable capacitor comprises a capacitor matrix component.
Embodiment 10. The power supply system of embodiment 1, further comprising:
 a vertically stacked structure comprising multiple circuit board layers,
 wherein the load is integrated on a top circuit board layer and the power amplifier is integrated on a lower layer of the vertically stacked structure.
Embodiment 11. The power supply system of embodiment 1, further comprising:
 a flat planar circuit board layer,
 wherein the load and the power amplifier are integrated on the flat planar layer.
Embodiment 12. A method comprising:
 interconnecting a power supply unit and a load,
 wherein the power supply unit comprises:
 a power amplifier,
 wherein the at least one power amplifier comprises:
 a transformer; and
 an inductor,
 wherein the power amplifier further comprises a variable capacitor in parallel with a transistor,
 wherein a resonance frequency of the transformer connected to the load is determined based on values of the inductor and the variable capacitor;
 receiving, at the transformer, a supply voltage at an operating frequency;
 outputting a supply power to the load at the operating frequency; and
 adjusting a capacitance value of the variable capacitor to match an impedance of the power amplifier with an impedance of the load.
Embodiment 13. The method of embodiment 12,
 wherein the capacitance value is adjusted to set a resonance frequency of the transformer connected to the load to match the operating frequency of the supply power.
Embodiment 14. The method of embodiment 12, further comprising:
 monitoring an operational parameter of the load and provide feedback to a controller; and
 controlling, via the controller, operation of the power amplifier based on the provided feedback.
Embodiment 15. A method of ozone generation comprising:
 providing a plasma actuator that generates ozone; and
 providing a circuit for driving the plasma actuator,
 wherein the circuit is:
 embedded in a wall with respect to which the plasma actuator is positioned; and
 driving the plasma actuator via the circuit to generate ozone.
Embodiment 16. The method of according to claim 15,
 wherein the circuit is horizontally or vertically stacked to fit within two cubic inch space, and
 wherein the ozone deodorizes, sterilizatizes, and/or decontaminates a region in which the ozone is generated.
Embodiment 17. The method of according to embodiment 16, wherein a shelf life of a fruit and/or vegetable in the region is extended by over 100%, with or without refrigeration.

Embodiment 18. A method comprising: interconnecting a power supply unit and a load, wherein the power supply unit comprises: a power amplifier, wherein the at least one power amplifier comprises: a transformer; and a fixed inductor, wherein the power amplifier further comprises a variable capacitor in parallel with a transistor, wherein a resonance frequency of the transformer connected to the load is determined based on values of the fixed inductor and the variable capacitor; receiving, at the transformer, a supply voltage at an operating frequency; outputting a supply power to the load at the operating frequency; and adjusting a capacitance value of the variable capacitor to match an impedance of the power amplifier with an impedance of the load.

Embodiment 19. The method of embodiment 1, wherein the capacitance value is adjusted to set a resonance frequency of the transformer connected to the load to match the operating frequency of the supply power.

Embodiment 20. The method of embodiment 1, further comprising: monitoring an operational parameter of the load and provide feedback to a controller; and controlling, via the controller, operation of the power amplifier based on the provided feedback.

Embodiment 21. A method of ozone generation comprising: a plasma actuator that generates ozone; and
 a circuit, wherein the circuit is engraved in the plasma actuator.

Embodiment 22. A method of deodorization and sterilization/decontamination, comprising: providing a circuit, wherein the circuit is horizontally or vertically stacked to fit within two cubic inch space.

Embodiment 23. A water purification device, comprising:
  a sediment filter that blocks larger contaminants from passing through and clogging the water treatment system;
  a Dielectric Barrier Discharge Ozone generator that generates ozone from air;
  a venturi injector that creates a pressure differential along the water trajectory, which sucks ozone generated by the ozone generator into the water stream, and subsequently mixes the ozone and water together;
  a mixing impeller that further mixes the ozone into the water flow;
  a reaction tank that allows the ozonated water to sit for a working period, allowing the ozone to destroy or precipitate the water contaminants; and
  a precipitate and ozone filter that filters out any remaining ozone before the treated water reaches the user and captures precipitate formed in the reaction with ozone, wherein the ozone eliminates or removes pathogens, microbes, metals, emerging contaminants, and pharmaceuticals from the water.

Embodiment 24. The device according to embodiment 23, wherein the ozone eliminates or removes viruses, fungi, and/or bacteria from the water.

Aspects of the invention may be described in the general context of computer-executable instructions, such as program modules, being executed by a computer. Generally, program modules include routines, programs, objects, components, data structures, etc., that perform particular tasks or implement particular abstract data types. Moreover, those skilled in the art will appreciate that the invention may be practiced with a variety of computer-system configurations, including multiprocessor systems, microprocessor-based or programmable-consumer electronics, minicomputers, mainframe computers, and the like. Any number of computer-systems and computer networks are acceptable for use with the present invention.

Specific hardware devices, programming languages, components, processes, protocols, and numerous details including operating environments and the like are set forth to provide a thorough understanding of the present invention. In other instances, structures, devices, and processes are shown in block-diagram form, rather than in detail, to avoid obscuring the present invention. But an ordinary-skilled artisan would understand that the present invention may be practiced without these specific details. Computer systems, servers, work stations, and other machines may be connected to one another across a communication medium including, for example, a network or networks.

As one skilled in the art will appreciate, embodiments of the present invention may be embodied as, among other things: a method, system, or computer-program product. Accordingly, the embodiments may take the form of a hardware embodiment, a software embodiment, or an embodiment combining software and hardware. In an embodiment, the present invention takes the form of a computer-program product that includes computer-useable instructions embodied on one or more computer-readable media.

Computer-readable media include both volatile and non-volatile media, transitory and non-transitory, transient and non-transient media, removable and nonremovable media, and contemplate media readable by a database, a switch, and various other network devices. By way of example, and not limitation, computer-readable media comprise media implemented in any method or technology for storing information. Examples of stored information include computer-useable instructions, data structures, program modules, and other data representations. Media examples include, but are not limited to, information-delivery media, RAM, ROM, EEPROM, flash memory or other memory technology, CD-ROM, digital versatile disks (DVD), holographic media or other optical disk storage, magnetic cassettes, magnetic tape, magnetic disk storage, and other magnetic storage devices. These technologies can store data momentarily, temporarily, or permanently.

The invention may be practiced in distributed-computing environments where tasks are performed by remote-processing devices that are linked through a communications network. In a distributed-computing environment, program modules may be located in both local and remote computer-storage media including memory storage devices. The computer-useable instructions form an interface to allow a computer to react according to a source of input. The instructions cooperate with other code segments to initiate a variety of tasks in response to data received in conjunction with the source of the received data.

The present invention may be practiced in a network environment such as a communications network. Such networks are widely used to connect various types of network elements, such as routers, servers, gateways, and so forth. Further, the invention may be practiced in a multi-network environment having various, connected public and/or private networks.

Communication between network elements may be wireless or wireline (wired). As will be appreciated by those skilled in the art, communication networks may take several different forms and may use several different communication protocols. And the present invention is not limited by the forms and communication protocols described herein.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

REFERENCES

1. Glowacz M, Rees D. Exposure to ozone reduces postharvest quality loss in red and green chilli peppers. Food Chem. 2016; 210:305-10.
2. Glowacz M, Rees D. The practicality of using ozone with fruit and vegetables. J Sci Food Agric. 2016; 96:4637-43.
3. Gertzou I N. Drosos P E, Karabagias I K, Riganakos K A. Combined effect of ozonation and packaging on shelf life extension of fresh chicken legs during storage under refrigeration. J Food Sci Tech. 2016; 53:4270-4277.
4. http://www.microbeworld.org/index.php?option=com_jlibrary&view=article&id=6401.
5. Mancinelli R L, McKay C P. Effects of nitric oxide and nitrogen dioxide on bacterial growth. Appl Environ Microbiol. 1983; 46:198-202.
6. Mastanaiah, N., Johnson, J. A., Roy, S. Effect of Dielectric and Liquid on Plasma Sterilization using Dielectric Barrier Discharge Plasma. *PLoS One* 8(8): e70840 (2013).
7. Mastanaiah, N., Banerjee, P., Johnson, J. A., Roy, S. Examining the role of Ozone in Surface Plasma Sterilization using Dielectric Barrier Discharge Plasma. Plasma Process Polymers (Cover Article). 2013; 10:1120-1133.
8. Swami S, Muzammil R, Saha S, Shabeer A, Oulkar D, Banerjee K, Singh S B. Evaluation of ozonation technique for pesticide residue removal and its effect on ascorbic acid, cyanidin-3-glucoside, and polyphenols in apple (Malus domesticus) fruits. Environ Monit Assess. 2016; 188:301.
9. Zelaya A J, Stough G, Rad N, et al. *Pseudomonas aeruginosa* Biofilm inactivation: Decreased cell culturability, adhesiveness to surfaces, and biofilm thickness upon high-pressure nonthermal plasma treatment. IEEE Trans Plasma Sci IEEE Nucl Plasma Sci Soc. 2010; 38:3398-3403.
10. Bollyky, J. (2002). Benefits of Ozone Treatment for Bottled Water. International Ozone Association Proceedings.
11. Bhatia et al. (2015) Treatment of Wastewater by Ozone Produced in Dielectric Barrier Discharge Journal of Chemistry, Article ID 648162, 6 pages. http://dx.doi.org/10.1155/2015/648162.
12. City of San Diego Water Quality Report 2017. https://www.sandiego.gov/sites/default/files/2017_quality_report_-_6-11-18_final.pdf.
13. VanBriesen, J. Potential Drinking Water Effects of Bromide Discharges from Coal-Fired Electric Power Plants.
14. Richardson, S. D., Thruston, A. D., Caughran, T. V. et al. (1999). Identification of New Ozone Disinfection Byproducts in Drinking Water. Environmental Science & Technology, 33 (19), 3368-3377.
15. Loeb, B. L., Thompson, C. M., Drago, J. et al. (2012) Worldwide Ozone Capacity for Treatment of Drinking Water and Wastewater: A Review, Ozone: Science & Engineering, 34:1, 64-77, DOI: 10.1080/01919512.2012.640251.
16. Langlais, B., Reckhow, D. A., & Brink, D. R. (Eds.). (1991). Ozone in water treatment: Application and engineering. Chelsea, Mich,: Lewis.
17. Schulz, C .R. (2014) Designing Integrated Ozone-Biofiltration Treatment Systems Ozone: Science & Engineering, 36: 276-286.
18. O'Donnell, C., Tiwari, B. K., Cullen, P. J., & Rice, R. G. (2012). Ozone in food processing. Chichester: Blackwell Publishing.
19. FDA (1982) GRAS status of ozone, Fed Reg, 47: 50 209-10.
20. The Measurement of Dissolved Ozone. https://www.chemetrics.com/image/data/product/pdf/Measurement_of_Ozone_White_Paper_Final.pdf.
21. S. Pekarek, "Non-Thermal Plasma Ozone Generation," Acta Polytechnica, vol. 43, no. 6], 2003.
22. M. Simek, S. Pekarek and V. Prukner, "Influence of power modulation on ozone production using an AC surface dielectric barrier discharge in oxygen," Plasma Chem Plasma Process, vol. 30, pp. 607-617, 2010.

The invention claimed is:

1. A method of treating water, comprising:
   interconnecting a power supply unit and a load,
   wherein the power supply unit comprises:
      a power amplifier, wherein the power amplifier comprises:
         a transfoiiiier;
         an inductor; and
         a variable capacitor in parallel with a transistor, wherein an inductance value of the inductor and a capacitance value of the variable capacitor are set based on a resonance frequency of the transformer connected to the load;
   receiving, at the power amplifier, a supply voltage;
   outputting, via the power amplifier, a supply power to the load at an operating frequency; and
   adjusting a capacitance value of the variable capacitor to adjust an impedance of the power amplifier when an impedance of the load changes;
   driving the load with the power supply unit to generate ozone; and
   exposing water to the ozone such that the ozone and water are mixed together and the ozone eliminates or removes pathogens, microbes, metals, emerging contaminants, and/or pharmaceuticals from the water.

2. The method of treating water according to claim 1, further comprising:
   monitoring an operational parameter of the load and providing feedback to a controller; and
   controlling, via the controller, operation of the power amplifier based on the feedback.

3. The method of treating water according to claim 1, wherein the power supply unit further comprises:
   additional circuitry to transform an alternating voltage from an electrical grid to a DC voltage delivered to the power amplifier.

4. The method of treating water according to claim 1, wherein the power supply unit further comprises:
   compartments and connections to attach batteries.

5. A method of deodorization and sterilization/decontamination, comprising:
   providing a circuit, wherein the circuit comprises a power supply unit and a load, wherein the power supply unit comprises:
      a power amplifier, wherein the power amplifier comprises:
         a transformer;
         an inductor; and
         a variable capacitor in parallel with a transistor, wherein an inductance value of the inductor and a capacitance value of the variable capacitor are set based on a resonance frequency of the transformer connected to the load, wherein the circuit is horizontally or vertically stacked to fit within a two cubic inch space.

6. The method of deodorization and sterilization/decontamination, according to claim 5, further comprising:
monitoring of environmental parameters, and providing feedback to a controlling unit; and
controlling, via the controlling unit, time of operation, and enabling and disabling of a power amplifier based on the feedback provided to the controlling unit.

7. A system of ozone generation, comprising:
a plasma actuator that generates ozone; and
a power supply circuit,
wherein the power supply circuit is engraved in the plasma actuator and supplies power to the plasma actuator
wherein the ozone eliminates or removes pathogens, microbes, metals, emerging contaminants, and/or pharmaceuticals from source water,
wherein the system further comprises:
a sediment filter that blocks larger contaminants from passing through and clogging the system;
a dielectric Barrier Discharge ozone generator that generates ozone from air;
a venturi injector that creates a pressure differential along a water flow of the source water, which sucks ozone generated by the dielectric Barrier Discharge ozone generator into the water flow, wherein the ozone and water are mixed together;
a mixing impeller that further mixes the ozone into the water flow to produce ozonated water;
a reaction tank that allows the ozonated water to sit for a working period, allowing the ozone to destroy or precipitate water contaminants in the ozonated water;
a precipitate and ozone filter that filters out ozone from the ozonated water and captures precipitate formed in the reaction of the ozonated water with the ozone.

8. The method of deodorization and sterilization/decontamination according to claim 5, further comprising: providing a system of ozone generation that is embedded in a wall of a sealed container, and powered by an external power supply and/or batteries.

9. The method of deodorization and sterilization/decontamination according to claim 5, further comprising: providing a system of ozone generation in a portable battery powered enclosure, wherein the system of ozone generation comprises a plasma actuator, where the plasma actuator and batteries are replicable, wherein enclosed ozone generation system is mounted on a wall or placed in a container for operation.

10. The method of deodorization and sterilization/decontamination according to claim 5, further comprising: providing a programmable timer for operation, an interface with sensors to deactivate system when a user is in a position to directly come into contact with generated ozone, and an interface LEDs to indicate operational state of the system.

11. The method of deodorization and sterilization/decontamination, according to claim 8, further comprising: providing a sensor to activate system when water flows through device.

12. The method of deodorization and sterilization/decontamination, according to claim 8, further comprising: providing a mixing impeller configured to generate electrical energy and an energy storage device configured to store such energy.

13. The method of deodorization and sterilization/decontaminationa according to claim 6, wherein the environmental parameters include ethylene, temperature, and humidity.

14. The system of ozone generation according to claim 7, wherein the ozone eliminates or removes viruses, fungi, and/or bacteria from the source water.

* * * * *

UNITED STATES PATENT AND TRADEMARK OFFICE
CERTIFICATE OF CORRECTION

PATENT NO. : 11,767,242 B2
APPLICATION NO. : 16/860523
DATED : September 26, 2023
INVENTOR(S) : Subrata Roy, Sherlie Eileen Portugal Atencio and Alexander Gustaw Schindler-Tyka It is certified that error appears in the above-identified patent and that said Letters Patent is hereby corrected as shown below:

In the Claims

Column 34,
Line 24, "transfoiiiier" should read --transformer--

Signed and Sealed this
Nineteenth Day of December, 2023

Katherine Kelly Vidal
*Director of the United States Patent and Trademark Office*